United States Patent [19]
dePinto et al.

[11] Patent Number: 5,365,428
[45] Date of Patent: Nov. 15, 1994

[54] DEVICE AND METHOD FOR REDUCING NUMBER OF DATA SAMPLE POINTS SENT TO A VIDEO DISPLAY SYSTEM

[75] Inventors: Victor M. dePinto, Kirkland, Wash.; Curtis D. Kinghorn, Ferguson, Mo.

[73] Assignee: Quinton Instrument Company, Seattle, Wash.

[21] Appl. No.: 822,781

[22] Filed: Jan. 21, 1992

[51] Int. Cl.$^5$ ............ G06F 15/42; A61B 5/0452
[52] U.S. Cl. ............ 364/413.06; 364/413.01; 128/696; 128/700; 128/703; 128/704; 128/705; 128/706; 128/702; 367/901; 382/6
[58] Field of Search ............ 364/413.06, 413.01, 364/413.13, 483, 486, 487; 382/6; 128/702, 696, 697, 670, 705; 367/901

[56] References Cited

U.S. PATENT DOCUMENTS

| | | | |
|---|---|---|---|
| 3,581,219 | 5/1971 | Alexander | 328/168 |
| 3,783,391 | 1/1974 | Hogg et al. | 328/111 |
| 3,897,774 | 8/1975 | Burdick et al. | 128/2.06 |
| 4,016,871 | 4/1977 | Schiff | 128/2.06 |
| 4,072,851 | 2/1978 | Rose | 364/487 |
| 4,170,992 | 10/1979 | Dillman | 128/702 |
| 4,296,755 | 10/1981 | Judell | 128/705 |
| 4,316,249 | 2/1982 | Gallant et al. | 364/417 |
| 4,559,602 | 12/1985 | Bates, Jr. | 364/487 |
| 4,596,255 | 6/1986 | Snell et al. | 128/697 |
| 4,832,038 | 5/1989 | Arai et al. | 128/670 |
| 5,092,341 | 3/1992 | Kelen | 128/702 |
| 5,109,862 | 5/1992 | Kelen et al. | 128/702 |

Primary Examiner—Roy N. Envall, Jr.
Assistant Examiner—Joseph Thomas
Attorney, Agent, or Firm—Andrew J. Beck; Montgomery W. Smith; Curtis D. Kinghorn

[57] ABSTRACT

A device is provided for reducing the number of ECG data sample points presented to a video display system to avoid overwhelming the video display screen with a number of ECG sample points and to present several seconds of data on the screen at the same time. The device ensures that the maximum and minimum values of the original ECG signal are displayed. A collection of consecutive points is broken into sub-groups which are each processed to produce representative amplitude values for each sub-group which representative values are then displayed on the display screen.

In the preferred embodiment, the device includes a microprocessor with electronic memory which calculates a representative amplitude value for each sub-group. The representative amplitude value is chosen depending on whether the sub-group contains a local maximum or a minimum in the values of consecutively sampled points or whether the data points of the sub-group are part of a curve leading to a local maximum or minimum. If the local minimum or maximum value of the sub-group appear between the end points of the sub-group, the maximum or minimum value of the sub-group is passed to the output depending on whether the curve is convex or concave shaped respectively.

23 Claims, 13 Drawing Sheets

DEVICE AND METHOD FOR REDUCING NUMBER OF DATA SAMPLE POINTS SENT TO A VIDEO DISPLAY SYSTEM

A portion of the disclosure of this patent document contains material which is subject to copyright protections. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The instant invention relates to a device for reducing the number of sample points presented to a video display device from a sampling system and more particularly to a device for reducing the number of sample points passed from an ECG processing system to a video display device while preserving the maximum and minimum values of the amplitudes of the ECG signal without causing distortion in the representative ECG signal.

2. Description of the Prior Art

In order to facilitate digital signal processing, the analog ECG signal produced by the heart and detected by an appropriate ECG detecting device is converted into a digital signal representative of the analog ECG signal. This digital signal is produced by sampling the analog ECG signal at prespecified time increments and recording the amplitude of the analog ECG signal at the particular time points. The greater the number of sample points measured per unit time, the greater the resolution of the corresponding digital signal. In particular, in order to accurately record the maximum and minimum amplitudes of the QRS portion of an signal, a high sample rate, typically 500 samples per second is used. It has been found that in the interval of one five hundredth of a second, the variation in the amplitude of the QRS signal is quite small. As a result, at a sample rate of 500 samples per second, the maximum and minimum amplitudes of the QRS signal are closely reproduced.

In typical video display devices, the graphic display screen consists of a display matrix having dimensions of 1000 pixels by 512 pixels. On such screens, it has been found useful to display about 9 seconds of ECG signals continuously on the screen for diagnostic purposes. If the EGG signal sampled at 500 samples per second is reproduced on such a display screen where the one thousand pixel axis corresponds to the time axis and if each sampled data point is reproduced on the display screen by an appropriately placed pixel, only two seconds worth of data could be displayed instead of the desired 9 seconds. Simple arithmetic shows that if 9 seconds worth of data points are to be displayed along the one thousands pixel time axis on the display screen, the number of data points presented to the display screen must be about 111 data points per second. Further arithmetic shows that if the rate of sending data points representative of the sampled ECG signal to the video display device of 500 data points per second is reduced by factor 2/9, this yields the desired display rate of about 111 data points per second. 111 data points per second will produce slightly more than 9 seconds worth of data on the display screen at one time.

FIG. 1 shows an ECG signal sampled at 500 samples per second. By comparison, FIG. 2 shows the same ECG signal sample at 111 samples per second. As can be seen, the lower sample rate produces an ECG trace with a reduced amplitude on the QRS complex.

In view of the foregoing, it is highly desirable to sample the analog ECG signal at a high sample rate such as 500 samples per second in order to accurately determine the maximum and minimum amplitudes of the QRS signals of an ECG signal. At the same time, it is highly desirable to send data points to the video display system at a reduced rate, as for example 2/9 of the sample rate of 500 data points per second, in order to present several seconds worth of sampling data on the display screen. Therefore, it is highly desirable to produce a device which converts the data collected at a high sample rate to data passed to the video display system at a lower rate while preserving an accurate representation of the originally monitored ECG signal. Specifically, it is highly desirable for the ECG trace produced by the video display system from data points passed to the video display system at a lower rate than the original sample rate of the ECG signal to accurately reproduce the maximum and minimum values of the ECG signal, particularly the QRS part of the ECG signal, despite the fact that fewer data points are used to represent the ECG signal.

SUMMARY OF THE INVENTION

A device is provided for reducing the number of ECG data sample points presented to a video display system to avoid overwhelming the video display screen with a large number of ECG sample points and to present several seconds of data on the screen at the same time. The device ensures that the maximum and minimum values of the original ECG signal are displayed. A collection of consecutive sample points is broken into sub-groups which are each processed to produce representative amplitude values for each sub-group which representative values are then displayed on the video display screen.

In the preferred embodiment, the device includes a microprocessor with electronic memory which calculates a representative amplitude value for each sub-group. The representative amplitude value is chosen depending on whether the sub-group contains a local maximum or a minimum in the values of consecutively sampled points or whether the data points of the sub-group are part of a curve leading to a local maximum or minimum.

Briefly stated, once a sub-group has been formed, the values of the end points are compared to the values of the other samples of the sub-group. If the values of the end points contain both the maximum and minimum values for the sub-group, this indicates that the values of the sub-group constitute a generally continuously rising or falling curve. In this case, the value of the middle sample point is chosen as representative of the value of the rising or falling curve. If, however, the maximum or minimum value of the sample group is found between the end points, this indicates that the sample points form a curve having either a generally convex or concave shape. Theoretically, this condition indicates that the first derivative of the curve formed by the sample points changes sign at some place between the end points. In order to determine whether such a curve is convex or concave, in the preferred embodiment, the second derivative of the curve formed by the sample points is found. If the value of the second derivative is less than zero, this indicates that the curve is convex. In this case, the maximum value of the sample group is passed to the data display system as the representative data point of the sample group. If the value of the second derivative is greater than zero, this indicates that the curve is concave. In this case, the minimum value of the sample group is passed to the data display system as the representative data point of the sample group.

DETAILED DESCRIPTION OF THE INVENTION

Figure 4:
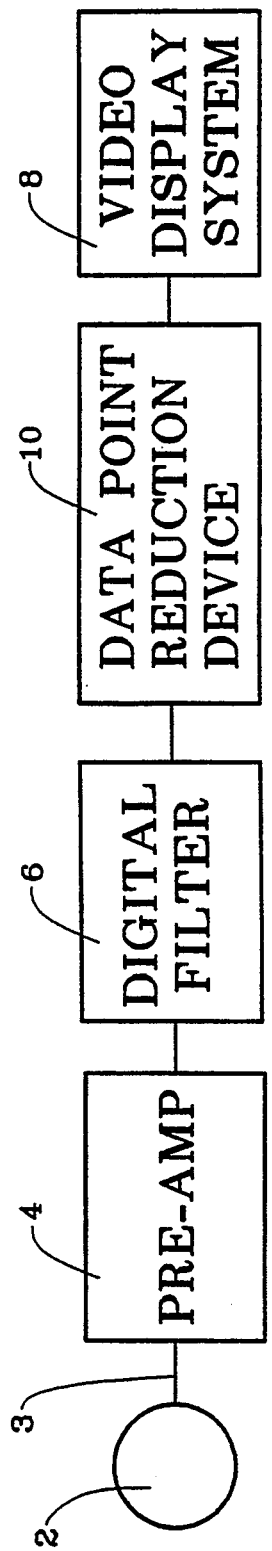
FIG. 4 is a block diagram of the instant invention.

As best shown in FIG. 4, the device for reducing the number of data sample points presented to a video display device is shown generally labeled 10. The device 10 is located in series with at least one electrode 2 attached to the patient and its corresponding ECG lead 3, pre-amp 4 and digital filter 6. A video display system 8 such as is common in the art, is attached to the output of the device 10. Electrode 2 is of the kind commonly used in ECG systems and is placed on the chest of the patient. ECG lead 3 is also of the type commonly used and connects electrode 2 to a pre-amp 4.

In pre-amp 4, the analog signal detected by the electrode 2 is converted to a digital signal through an A to D converter. Pre-amp 4 actually samples the ECG signal at a rate of 2000 samples per second. As such, it is an effective anti-aliasing filter which has a Nyquist point of 1000 Hertz. Every four sample points are averaged together to produce a representative sample point for the four samples so the 2000 samples per second sampling rate produces a digital output signal of 500 samples per second. By averaging every four consecutive samples together, the high frequency noise is reduced. Further, processes such as eliminating any D.C. signal component and amplifying the signal are performed at pre-amp 4.

The resulting digital signal is then passed from pre-amp 4 to digital filter 6 for digital filter processing. This digital filter processing may be the removal of base line wander as is described in U.S. Pat. No. 5,269,313 or may be a muscle artifact filter as described in U.S. Pat. No. 5,259,387.

The signal, having been passed through digital filter 6, is then presented to the input of device 10. As stated, the device 10 is in turn connected to a video display system 8 which typically stores collected digital sample points from device 10 in a video buffer to be displayed on a video display terminal. The video display terminal typically has a display field of 1000 by 512 pixels, although other configurations for the display field are possible. The 1000 pixel axis typically extends in the horizontal direction and represents the time axis. The vertical axis has 512 pixels and represents the amplitude of the ECG signal.

As explained above, it is desirable when sampling a signal at a high sample rate to produce a digital signal at a lower sample rate to be passed to the video display system 8 to avoid overwhelming the video display system 8 and to display many seconds of the ECG signal at one time. For example, when sampling at a sample rate of 500 samples per second, it is desirable to produce a digital signal for input to the video display system 8 at 2/9 this rate. In other words, for every nine input samples, two output samples are passed to the video display system 8.

Figure 5:
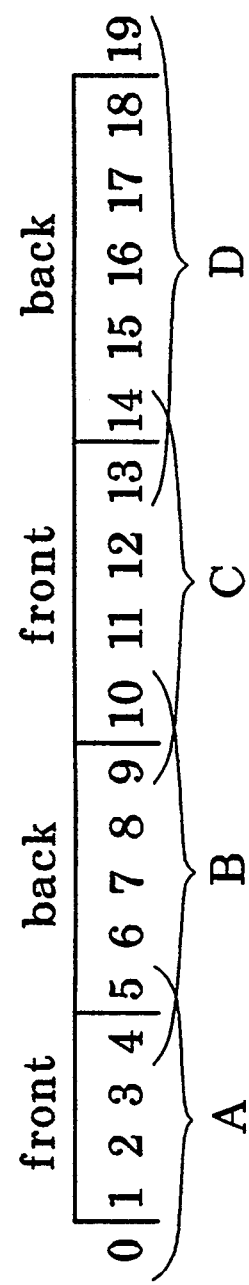
FIG. 5 shows a series of consecutive data points arranged into sub-groups.
Figure 6A:
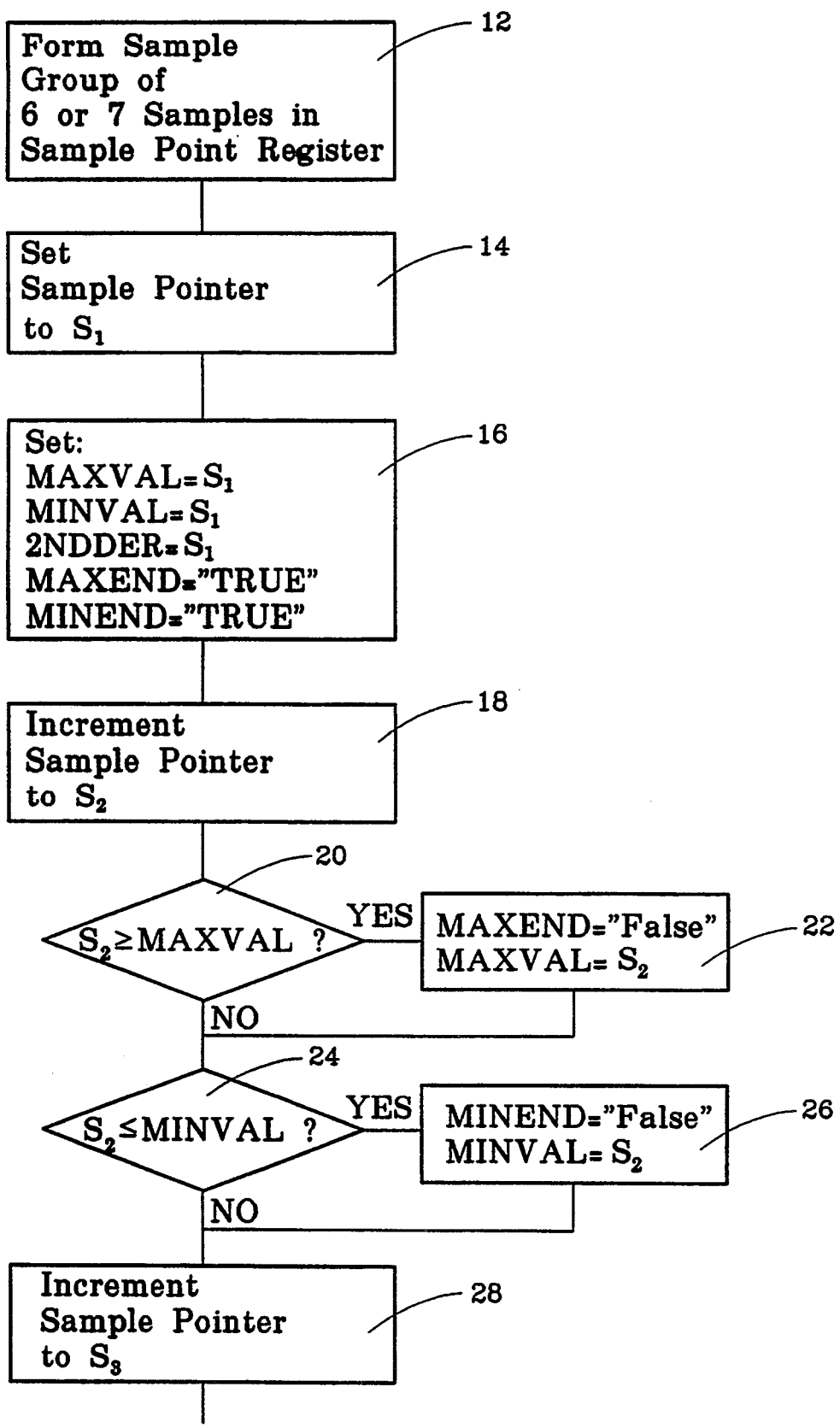
FIGS. 6A-E are a flow chart showing the preferred embodiment of the software of the invention.
Figure 6B:
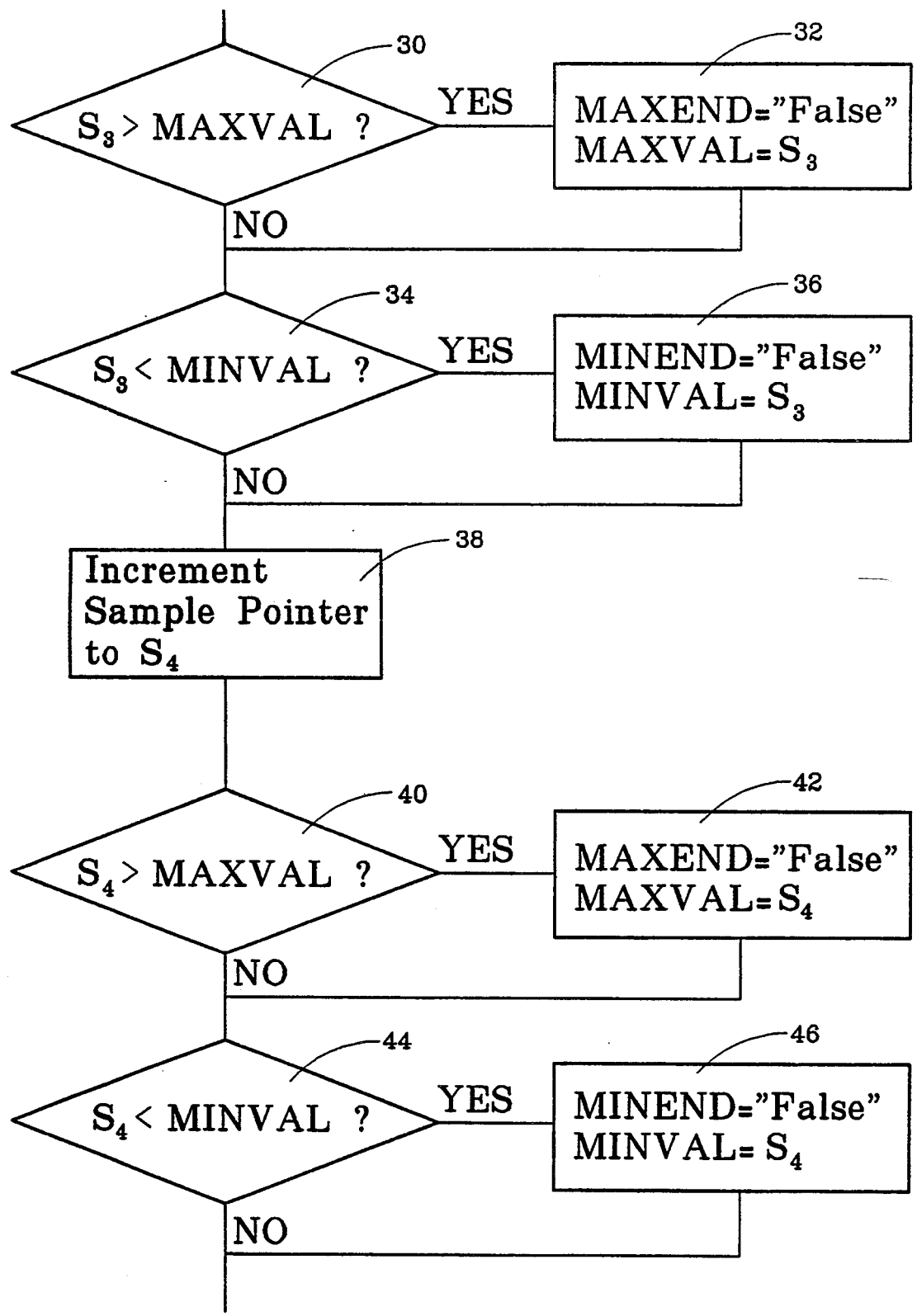
Figure 6C:
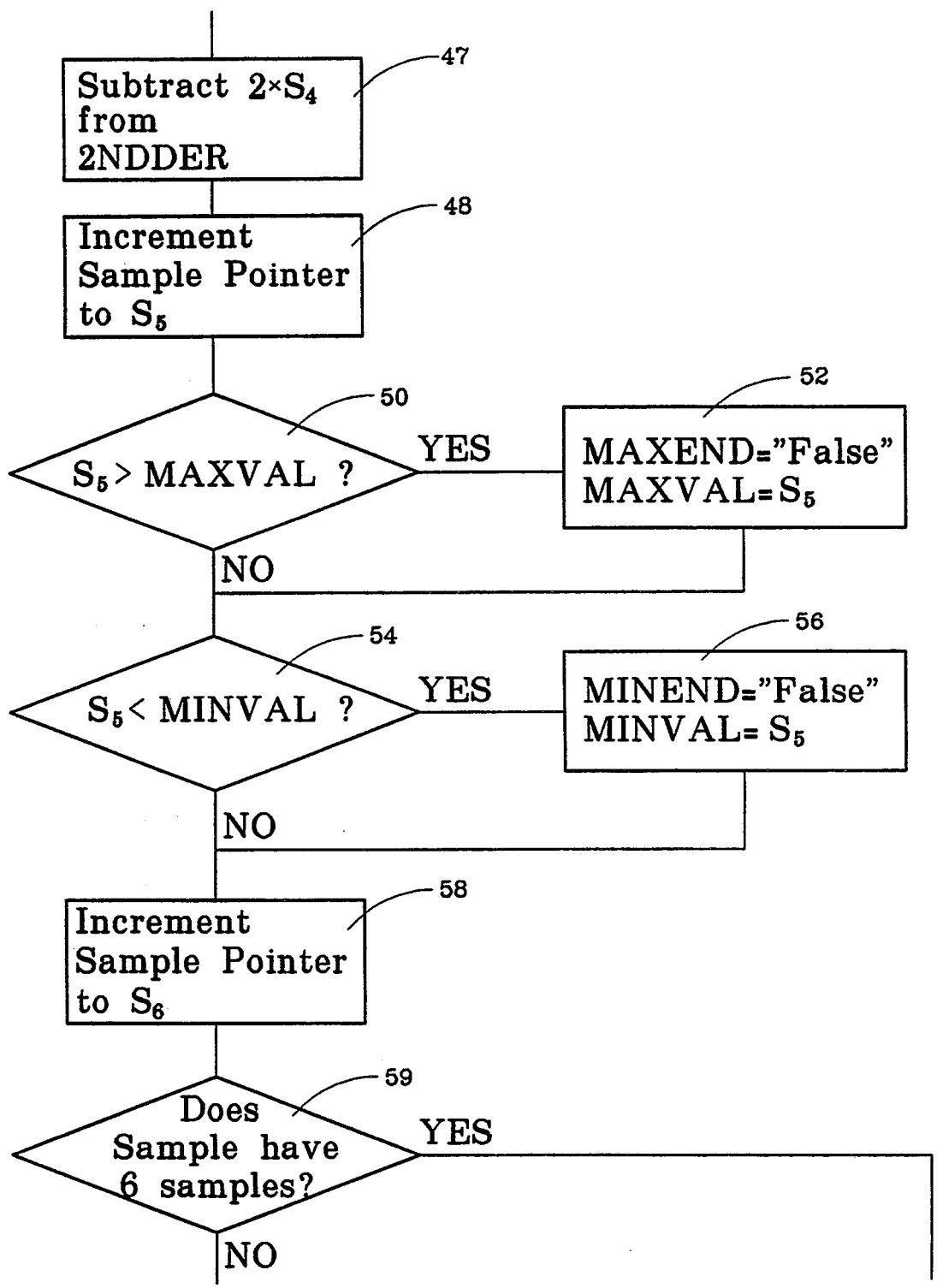
Figure 6D:
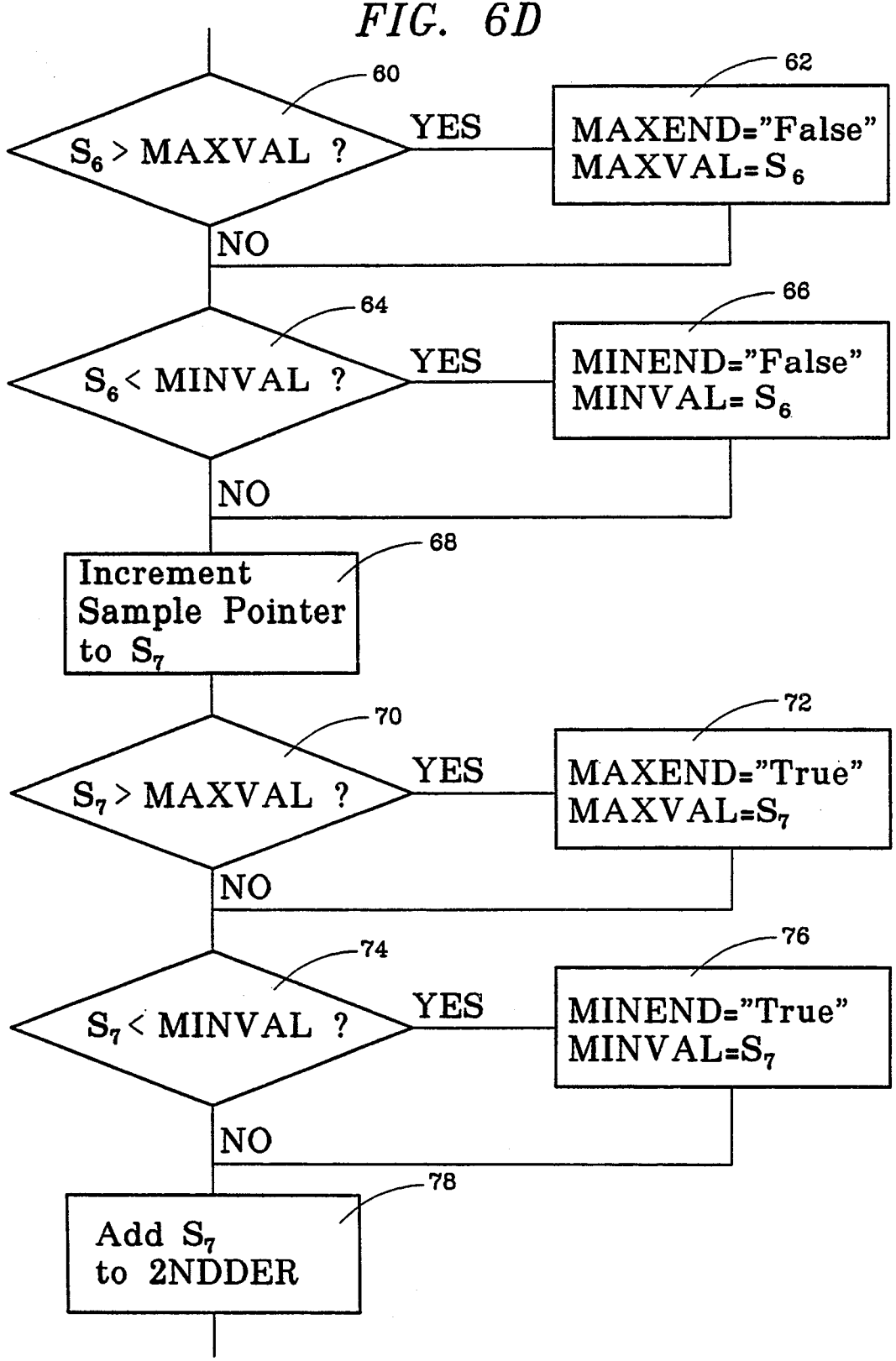
Figure 6E:
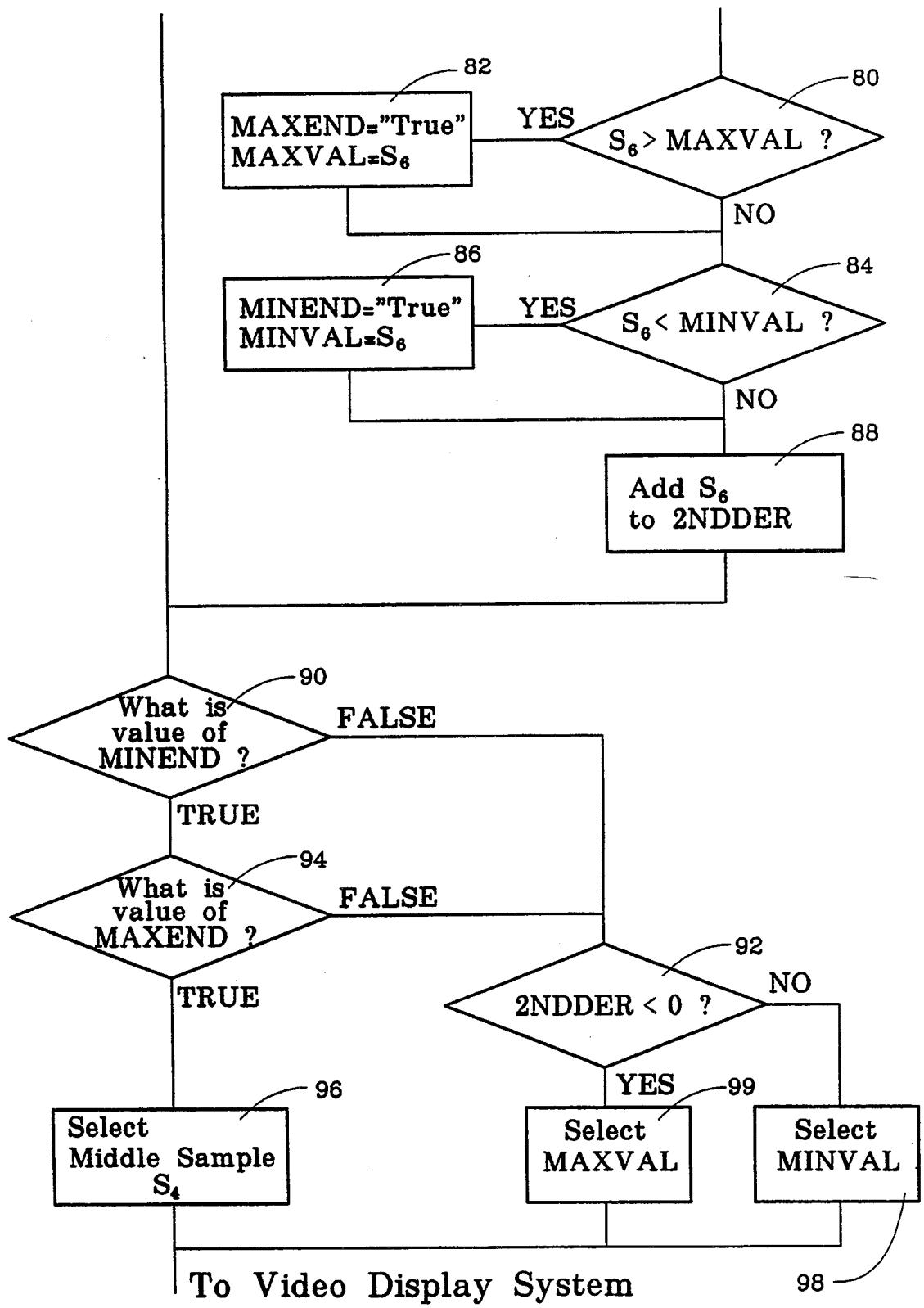

FIG. 5 shows a series of consecutive samples numbered "0" through "19". The consecutive samples are representative of any group of consecutive samples from an ECG signal presented to the input of the device 10. Each nine consecutive sample points are divided into two groups labeled "front" and "back". Each group will have a representative value which will be passed to the video display device 8. As can be seen, each "front" and "back" group corresponds to a sub-group such as A, B, C which sub-group overlaps the preceding and subsequent "front" and "back" groups by one sample point in each direction. This ensures a smooth continuity of representative output values produced from one sub-group to the next.

In the preferred embodiment of the instant invention, sub-group A encompasses the first four sample points labeled "1" through "4" of the "front" group. Sub-group A is extended by one sample point on each side of the "front" group to include sample point "0" and sample point "5" so that sub-group A contains six consecutive sample points. Sub-group A is extended to include sample points "0" and "5" so that sub-group A will overlap the preceding and subsequent "front" and "back" groups.

Sub-group B corresponds to the "back" group which encompasses sample points "5" through "9". Sub-group B overlaps the "front" group of sub-group A by one sample point so that sample point "4" is included in sub-group B. Sub-group B is also extended by one to include sample point "10" so that sub-group B overlaps the subsequent "front" group at sample point "10". Sub-group B then includes seven sample points from sample points "4" through "10".

Continuing in the same progression, sub-group C corresponds to the "front" group of the next nine sample points and encompasses the four sample points "10" through "13" of that "front" group. But, sub-group C overlaps the immediately preceding "back" group by one so that the sample point "9" is included Additionally, sub-group C overlaps the subsequent "back" group by one so that sample point "14" is also included. Sub-group C then has six sample points from "9" to "14". A process similar to that described above produces a sub-group D corresponding to the second "back" group and having seven sample points from "13" to "19".

This pattern of developing sub-groups having alternating six and seven samples corresponding to "front" and "back" groups continues through the sampling sequence. Each sample sub-group will produce a representative value which will be passed from the device 10 to the video display system 8 to be displayed. Of course, if consecutive samples of more or less than 9 sample points is desired to be processed to produce a desired number of representative samples, various combinations and sizes of sub-groups may be formed. For example, if a series of 8 consecutive sample points is desired to produce two representative values, the "front" and "back" groups would each have four sample points contained therein so that each sub-group A, B, C, etc. would then have six sample points.

Further, if 9 consecutive sample points are desired to be reduced to three representative values, the 9 consecutive sample groups could be broken into groups of three consecutive sample points so that the corresponding sub-groups would then each have five sample points. As can be seen, many variations in both the number of consecutive sample points and the number of representative data points produced therefrom can be processed by the teachings of the instant invention. Throughout this application, the illustrative example used to explain the invention will consist of 9 consecutive sample points divided into a "front" group of 4 samples and a "back" group of 5 samples from which a representative sample will be produced from each sub-group corresponding to the "front" and "back" groups.

With reference now to FIGS. 6A-E, the preferred embodiment of the flow chart of the software used in the device 10 is shown. The software is preferably implemented on a microprocessor or similar device which has electronic memory capable of forming memory registers. In step 12, a sample group consisting of either six or seven sample points from a sub-group as described above is formed. These six or seven sample points are placed in a sample point register having addresses S1 through S7 with the oldest sample point placed in address S1 and with the newest sample point placed in address S6 or S7 depending on the size of the sample group. The program then passes to Step 14 which points the sample pointer to address S1. After the sample pointer has been pointed to address S1, the program passes to step 16.

Besides the sample point register described above, five registers are used in the software. A register entitled "MAX VAL" will ultimately contain the maximum value of the samples contained in the sample group. A register labeled "MIN VAL" will ultimately contain the minimum value of the samples in the sample group. Registers "MAX END" and "MIN END" are boolean registers which will contain the value "true" if the maximum or minimum value respectively of the sample group is found at one or the other end points, S1 or S6/S7, of the sample group A register "2ND DER" which stands for "second derivative", will eventually contain the value of the second derivative of the sample group. In step 16, these registers are initialized. Registers "MAX VAL" and "MIN VAL" are initialized to contain the value of the sample stored at S1. Registers "MAX END" and "MIN END" are initialized to contain the value "true". Further, the register "2ND DER" is initialized to contain the value of S1.

After the registers have received their initial values in step 16, the program passes to step 18. Step 18 increments the sample pointer to point at sample S2 and passes the program to step 20. Step 20 asks whether the value stored S2 is greater than or equal to the value stored in register "MAX VAL". If S2 is larger than or equal to the value stored in "MAX VAL", it is clear that the maximum value of the sample group does not uniquely appear at the first end point. If S2 is larger than the value stored in "MAX VAL" the maximum value of the sample group does not appear at S1. If S2 has a value equal to the S1, then the maximum value of sample group may be at both S1 and S2. Therefore, the boolean indicator in "MAX END" is changed to "false" as indicated in step 22. Although the end point contained in either S6 or S7 may contain the maximum value for the sample group, and therefore change the boolean value in register "MAX END" to true, this determination will be made later in the program. For the mean time, if S2 is larger than or equal to the value stored in "MAX VAL" which will be the value of S1 at this time, the register "MAX END" will contain the value "false". In addition in step 22, the register "MAX VAL" is updated to contain the new maximum value which is found in register S2. Thereafter, the program passes from step 22 to step 24.

In step 20, if the value of S2 is not greater than or equal to the value of "MAX VAL", in other words the value of S2 is less than the value of "MAX VAL" which now contains the value of S1, the program passes to step 24.

Step 24 asks whether S2 is less than or equal to the value of register "MIN VAL". If the answer to the question of step 24 is "yes", then it is clear that the minimum value of the sample group is not at the first end point. The program then passes to step 26 where the boolean value in "MIN END" is changed to "false". By analogy to the description above where the value "false" is placed in register "MAX END" in step 22 despite the possibility that the maximum value of the sample group may be found at the end point S6 or S7, step 26 places the boolean value "false" in register "MIN END" despite the possibility that the minimum value of the sample group will be found at the end point S6 or S7. Further, step 26 updates register "MIN-VAL" to contain the value stored in register S2. Thereafter, the program passes from step 26 to step 28. If S2 is not than or equal to the value of register "MIN VAL", in other words, if S2 is greater than the value in "MIN VAL", the program passes from step 24 to step 28.

Step 28 increments the sample pointer from S2 to S3. Steps 30 through 38 are then performed. Steps 30 through 38 are identical to corresponding steps 20 through 28 with three exceptions as explained hereafter. Steps through 38 correspond to steps 20 through 28 by adding ten to the reference numbers of steps 20 through 28, Throughout this description reference will be made to corresponding steps. By correspondence it is to be understood that a first step corresponds to a second if the first step has a reference number which is an even multiple of ten larger than the second step.

The three exceptions to the identity between steps 20 through 28 and steps 30 through 38 are: "S2" in steps 20 through 28 is replaced with "S3" in the corresponding steps 30 through 38; the "greater than or equal to" and "less than or equal to" relationships of steps 20 and 24 respectively are replaced with strict "greater than" and "less than" relationships in steps 30 and 34 respectively; and, the sample pointer in step 38 is incremented to point to S4 rather than S3 as in step 28. The reason that the greater than or equal to, and less than or equal to symbols in steps 20 through 28 are replaced with the strictly greater than or strictly less than symbols, respectively, is that in steps 30 through 38, if the compared values are equal, the registers "MAX VAL" and "MIN VAL" will already contain the highest and lowest value, respectively, found by the program so far. Therefore, in order to avoid replacing the value in "MAX VAL" and "MIN VAL" with the same value already contained therein, the program in steps 30 through 38 uses the strict greater than and strict less than relationship. Further if the value of S3 is equal to the value of S2, the values of "MAX END" and "MIN END" would not change. Therefore, there is no need to replace the values in "MAX END" and "MIN END" with the same values at steps 32 and 36. The use of the strict "greater than" and "less than" relationship in steps 30 and 34 avoids the microprocessor having to do redundant operations.

Steps 40 through 46 are identical to steps 30 through 36 with the difference that "S3" in steps 30 through 36 is replaced with "S4" in the corresponding steps 40 through 46. After step 46, the program passes to step 47. In step 47 the value of S4 is multiplied by 2 and then subtracted from the value in register "2ND DER". S4 represents the middle sample of the sample group despite whether the sample group contains six or seven samples. The choice of S4 as the representative value of the middle sample of both a 6 and a 7 sample group is explained in more detail in the description of step 96 hereafter. The program then passes to step 48 which increments the sample pointer to point at S5.

From step 48, the program passes to steps 50 through 58 which are identical to steps 30 through 38 with the difference that "S3" in steps 30 through 38 is replaced with "S5" in the corresponding steps 50 through 58, and the sample pointer is incremented to "S6" in step 58 instead of to "S4" as in step 38.

From step 58, the program passes to step 59 which directs the program depending on whether the sample group consists of six or seven elements. Step 59 asks whether the sample size is 6 If the answer is "yes" the program passes to steps 86 through 88. If the answer is "no", the program passes to steps 60 through 78. The reason there are two separate program paths from step 59 depending on the size of the sample group is that steps 70 through 78 and steps 80 through 88 perform comparisons and set boolean relation flags according to whether the end point of the sample group is S7 or S6 respectively. If the sample group has 7 sample points, S6 is one of the sample points between the end points. As such, S6 must be compared to the values of registers "MAX VAL" and "MIN VAL" with the consequent update of these registers and registers "MAX END" and "MIN END" as was done with sample points S2 through S5. Steps 60 through 68 perform this function. Steps 60 through 68 are identical to corresponding steps 30 through 38 with the difference that "S3" in steps 30 through 38 is replaced with "S6" in the corresponding steps 60 through 68 and the sample pointer is incremented to "S7" in step 68 instead of "S4" as in step 38.

As indicated above, if the sample size contains seven elements, step 59 passes the program to steps 60 through 68. From step 68, the program passes to step 70. Steps 70 through 78 compare the value of S7 to the various registers and set boolean relations based on the fact that S7 is an end point and not a point between the end points. Consequently, if S7 has the largest or smallest value of the sample group, the boolean value of registers "MAX END" and "MIN END" respectively is changed to "true".

In operation, step 70 asks whether the value of S7 is larger than the value of "MAX VAL". If the answer is "yes" the maximum value of the sample group appears at the end point. Therefore, the program is passed to step 72 which sets the boolean value of "MAX END" at "true". In addition, step 72 updates "MAX VAL" to contain the value of S7. Thereafter, the program passes from step 72 to step 74.

If, in step 70, the value of S7 is not larger than "MAX VAL" in other words, if S7 is less than or equal to the value in "MAX VAL" the program passes to step 74. Step 74 asks whether S7 is less than the value of "MIN VAL". If the answer is "yes", this indicates that a minimum of the sample group appears at the end point. Therefore, the program passes to step 76 where the boolean value of "MIN END" is changed to "true". In addition, step 76 updates the value of "MIN VAL" to contain the value of S7. Thereafter, the program passes to step 78. If, at step 74, S7 is greater than the value of "MIN VAL" the program passes to step 78.

Step 78 adds the value of S7 to the register "2ND DER". Therefore, register "2ND DER" now contains the calculated value of the second derivative of the sample group according to the formula:

i Second derivative = $S1 - 2 \times S4 + S7$.

Thereafter, the program passes from step 78 to step 90.

If the answer to the question of step 59 is "yes", the sample group contains 6 samples. The program is then directed to steps 80 through 88. Steps 80 through 88 are identical to corresponding steps 70 through 78 in form and function with the difference that "S7" in steps 70 through 78 is replaced throughout steps 80 through 88 with "S6". The program then passes to step 90.

As stated, the software determines a representative value for the sub-groups A,B, C, etc. which will be passed to the video display system 8. Steps 90 through 99 determine these representative values based on the relationship between the values of the samples as described above. Step 90 asks whether the value in register "MIN END", which indicates whether the minimum value of the sample group appears at one of the end points, contains the boolean value "true" or "false". If the value in register "MIN END" is "false", indicating that the minimum value of the sample group is not found at one of the end points, the program passes to step 92. If register "MIN END" contains a "true", indicating the minimum value of the sample group is found at one of the end points, the program passes to step 94.

Step 94 asks whether the boolean value in register "MAX END", which indicates whether the maximum value of the sample group occurred at an end point, is "true" or "false". If register "MAX END" contains the value "false", indicating that the maximum value of the sample group is not found at an end point, the program passes to step 92. If register "MAX END" contains the value "true", indicating that the maximum value of the sample group is found at an end point, the program passes to step 96.

In order for a program to have passed to step 96, the sample group must have had a minimum value at one end point and a maximum value at the other end point. This indicates a segment of the ECG signal which is either generally continuously rising or falling. When this occurs, step 96 selects the middle sample, S4, as the representative value for the sample group and passes this value to a video display system 8.

As can be seen, step 96 selects the middle sample, S4, as the representative value for the sample group. In the case where the sample group has seven sample points, S4 is clearly the middle sample for the sample group. However, in the case where the sample group has six sample points, the true center of the sample group lies between S3 and S4. However, in the preferred embodiment, the value of S4 is still chosen as the representative sample point. However, if desired, the value of S3 and S4 can be added together and divided by 2 to produce a representative value. Experience has shown that the representative value obtained by adding S3 and S4 and dividing by 2 does not differ appreciably from the value of S4 because of the signal's inability to rapidly change in the time interval between samples of 1/500th of a second. Further, the process of adding S3 and S4 and dividing by 2 comprises additional computing steps which are avoided by simply choosing S4 as the representative value.

In order to get to step 92, the sample group must not have a minimum at one end point or if it does have a minimum at one end point, it must not also have a maximum at the other end point. In other words, either a minimum or maximum value of the sample group occurs at a sample point between the end points. A curve formed by a line graphically connecting consecutive sample points of the sample group must somewhere have a zero slope. This means that a curve formed from graphically connecting consecutive sample points will have either a concave or convex shape. The second derivative of such a curve will determine whether the resulting curve is concave or convex depending on whether the sign of the second derivative is positive or negative respectively.

Therefore, step 92 asks whether the second derivative of the sample group, as calculated and stored in register "2ND DER" is less than zero. The second derivative is calculated as explained above, by taking the oldest sample point, subtracting two times the middle sample point and thereafter adding the newest sample point. In the embodiment described above, the second derivative is calculated in pieces as the program passes from step 16 to step 78 or step 88 depending on the size of the sample group. However, since the value of the second derivative is needed only if the program passes to step 92 as described above, the value of the second derivative may be calculated at one time immediately prior to passing to step 92 from steps 90 or 94. If the second derivative is to be calculated in this way, it need not be calculated in pieces as the program passes from step 16 to steps 77 or 88 as described above.

If in step 92, the second derivative is not less than zero, that is, the value in "2ND DER" is either equal to or greater than zero, this indicates that the curve resulting from connecting the sample group together is flat or concave respectively. In this case, the program passes to step 98 where the value stored in register "MIN VAL", which represents the minimum value of the sample group, and also the minimum value of the concave curve, is passed to the video display system 8.

If, according to step 92, the value of the second derivative stored in register "2ND DER" is less than zero, this indicates that the curve resulting from graphically connecting consecutive sample points is convex. Therefore, the program passes to step 99 where the value stored in the register "MAX VAL" which indicates the maximum value of the sample group, is passed to the video display system 8.

It is possible for the sample group to contain a curve having two places where the first derivative is equal to zero. According to the present invention, when this occurs, the program will pass to either step 92 or step 96. In the first case, the program passing to step 92, the second derivative may be either positive or negative, depending on the values of the sampled points. This variability results from the fact that if the sample group has such a curve, the variability is not from the ECG signal, which does not have such variance in the interval represented by the sample group, typically 6 to 7/500ths of a second. Instead, such a curve results from noise accompanying the ECG signal. Since such a curve results from noise, which is random, the curve will typically not have much variance in amplitude along the sample group. Therefore, whether the second derivative is positive or negative, with the resulting passing of the maximum or minimum value of the sample group to the video display device 8, will not significantly distort the representative signal passed to the video display device 8 from the device 10. In effect, the value passed to the video display device 8 in this case, represents a sort of mathematical averaging of the noise present in the ECG signal over the sample group.

In the second case, where the curve representative of the sample group has two places where the first derivative is zero and the program passes to step 96, the curve must have a minimum value at one end point and a maximum value at the other. Once again, the variability between end points results from noise present with the ECG signal and not from variability in the ECG signal itself. In this case, step 96 passes the value of the middle sample S4 to the video display system 8. This middle value S4 represents a sort of average of the sample group between the two end points.

Figure 7:
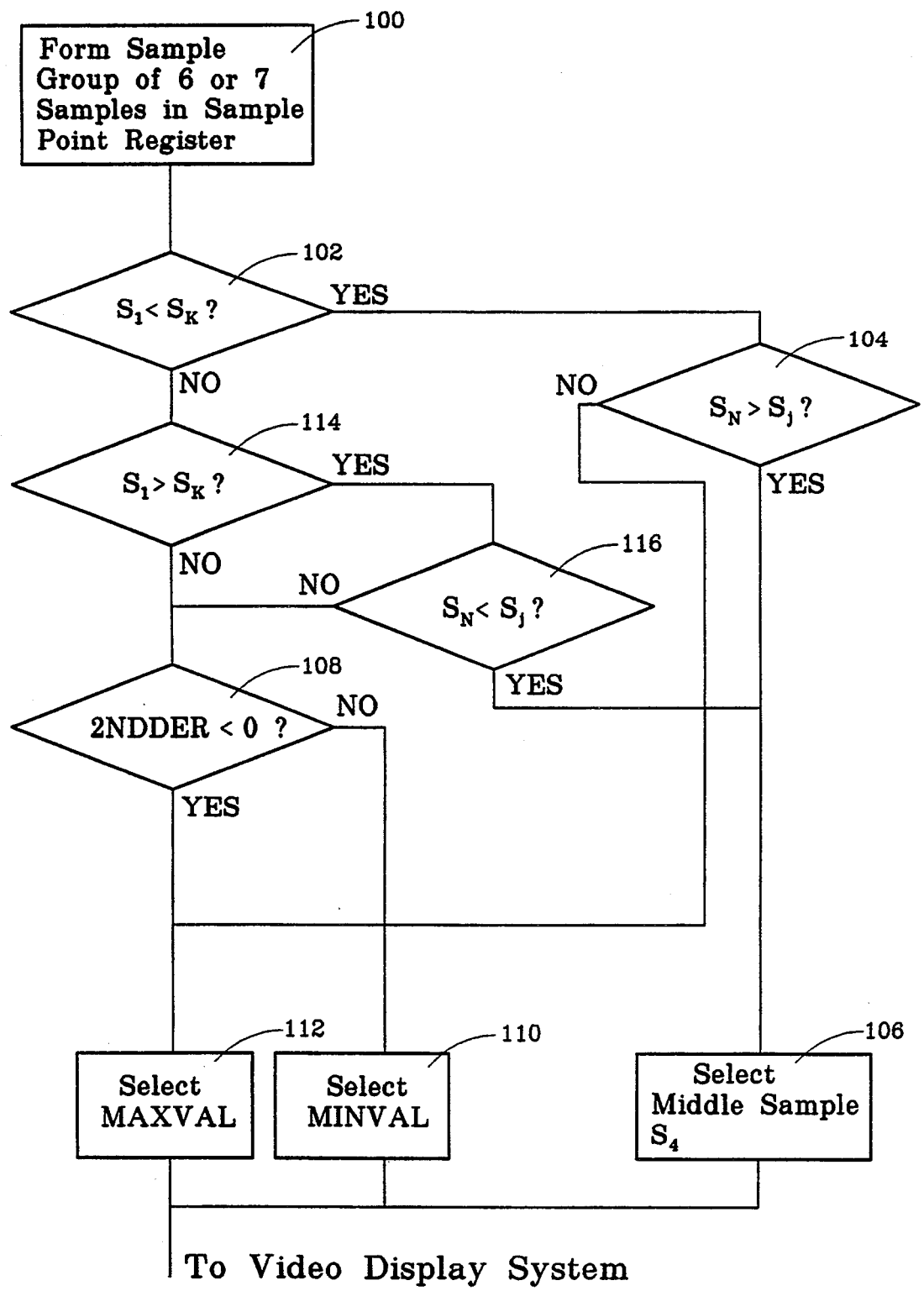
FIG. 7 is a flow chart showing an alternate embodiment of the software of the invention.

FIG. 7 shows an alternate flow chart for selecting representative values of the sample group to pass to the video display system 8. Step 100 forms a sample group of either six or seven sample points as described above in detail in connection with the description of step 12. Thereafter, the program passes to step 102.

In step 102, the value of S1 is compared to the value of all the other samples denoted by $S_K$ where K varies from 2 to 6 when the sample group has 6 sample points and from 2 to 7 when the sample group has 7 sample points. If the value of S1 is less than the value of any of the other samples $S_K$, indicating that S1 is the minimum of the sample group, the program passes to step 104.

Step 104 asks whether the newest sample point $S_N$, representing either S6 or S7 depending on the size of the sample group, is greater than all the other sample points denoted by $S_j$ where j varies from 1 to 5 when the sample group has 6 sample points and from 1 to 6 when the sample group has 7 sample points. If $S_N$ is greater than all the other sample points $S_j$, this indicates that the newest sample point $S_N$ is the maximum of the sample group. Further, since one end point, S1, is the minimum and the other end point, either S6 or S7 is the maximum, the curve of consecutively graphically connected sample points is a generally continuously upward directed curve. When this occurs, the program passes to step 106 which passes the value of S4 the middle sample point, to the video display system 8. Once again, the value of register S4 is passed to the video display system 8 as the representative value of the middle of the sample group whether the sample group has 6 or 7 samples as described above in connection with the description of step 96.

If the newest sample point $S_N$, either S6 or S7, is not greater than the other samples in step 104, in other words, $S_N$ is less than or equal to $S_j$, this indicates the representative curve of the sample group is a generally convex shaped curve. The program then passes to step 112 which passes the maximum value of the sample group which represents the maximum value of the convex curve, to video display system 8.

Returning to step 102, if the value of the sample point S1 is not less than any other sample $S_K$, in other words is not the minimum of the sample group, then the program passes to step 114. In step 114, it is determined whether the value of S1 is greater than, or the maximum of, any of the other sample points $S_K$. If the value of S1 is not greater than any of the other samples $S_K$, as determined in step 114, this indicates that the representative curve is generally concave shaped and the program passes to step 108.

In step 108, the derivative of the sample group is calculated according to the following equations:

For a sample group containing 7 points, the second derivative is determined as follows:

$$2nd\ derivative = S1 - 2 \times S4 + S7$$

For a sample group containing 6 points, the second derivative is determined as follows:

$$2nd\ derivative = S1 - S3 - S4 + S6$$

As can be seen, the general formula for determining the second derivative is:

2nd derivative = the value of one end point + the value of the other end point − 2 times the value of the middle sample.

Step 108 then determines whether the value of the second derivative is less than zero. If the value of the second derivative is not less than zero, in other words, the value of the second derivative is greater than or equal to zero, this indicates a generally concave or flat curve respectively. In this case, the program passes to step 110 which passes the minimum value of the sample group to the video display system 8.

If the value of the second derivative is less than zero, this indicates that the resulting curve is a generally convex curve. In this case, the program passes to step 112 which passes the maximum value of the sample points to the video display system 8.

Returning to step 114, if S1 is greater than any of the other samples $S_K$, this indicates that the representative curve extends generally downward from S1 and the program passes to step 116. Step 116 asks whether the newest value $S_N$, S6 or S7, of the sample group is less than any of the other sample points $S_j$. If the answer is "yes", this indicates that the curve is a generally continuous downward curve from the point S1 to the newest sample $S_N$, either S6 or S7. Therefore, the program passes to step 106 where the middle value S4 is passed to the video display system 8. S4 is passed as the representative value whether the sample group has 6 or 7 samples as explained above in connection with the description of step 96.

If, in step 116, the value of the newest sample point $S_N$, S6 or S7, is not less than the other samples $S_j$, this indicates a generally concave curve. In this case, the program passes to step 108 whereafter the program will be passed to either step 110 or step 112 to pass a representative value for the sample group to the video display system 8 as described in detail above in connection with the description of steps 110 and 112.

Figure 8:
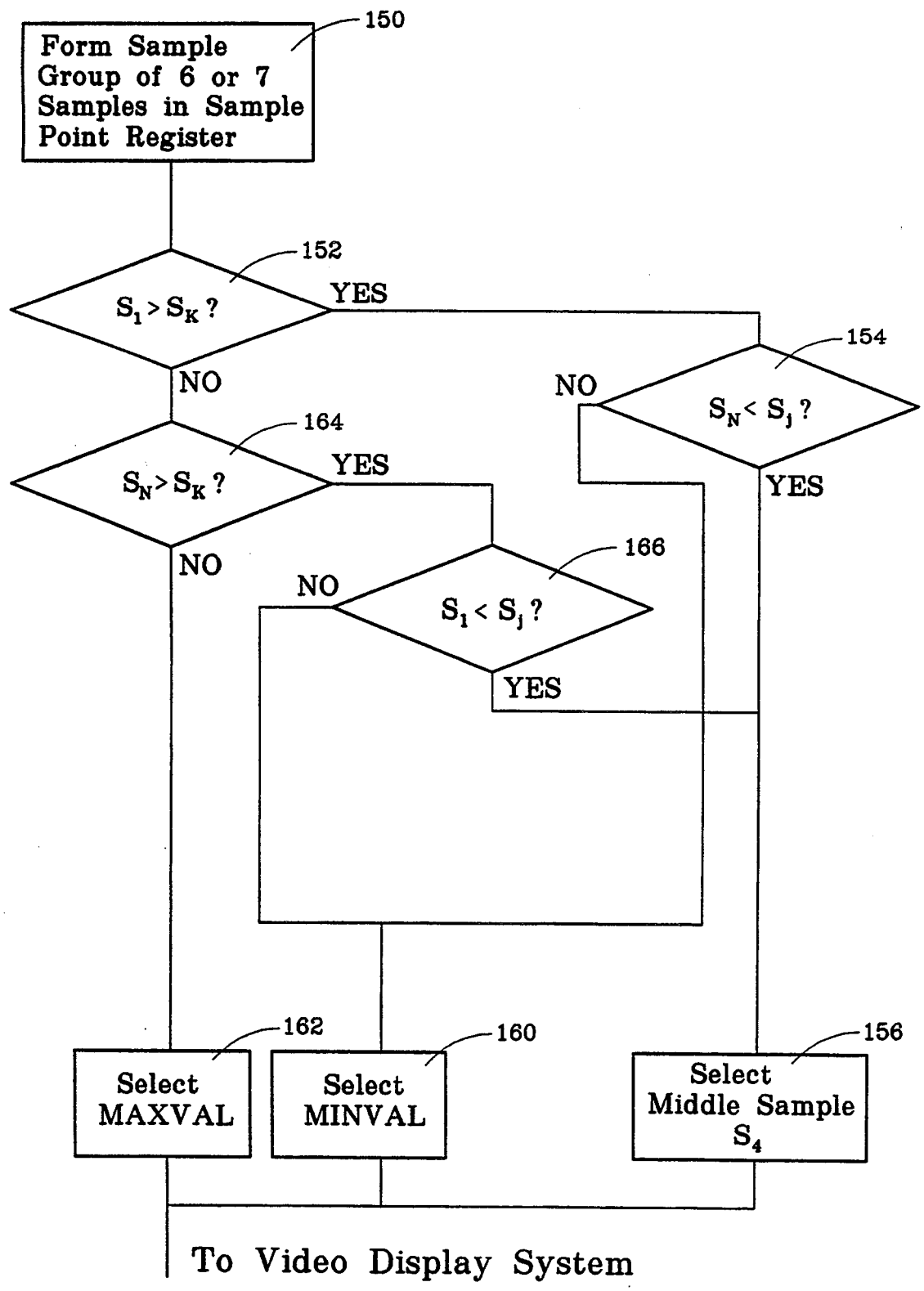
FIG. 8 is a flow chart showing another alternate embodiment of the software of the invention.

Yet another embodiment of the instant invention is shown in FIG. 8 which shows a flow chart for implementing the software system of this alternate embodiment. In this embodiment, the program begins at step 150 where a sample group of sample points from subgroup A, B, C, etc. consisting of either 6 or 7 sample points as described above in connection with the description of step 12 are stored in a memory register. These sample points are labeled S1 through S6 or S1 to S7 depending on whether the size of the sample group is six or seven sample points respectively. The program then passes to step 152 where it is determined whether the sample stored in register S1 is greater than, or the maximum of, any other sample point $S_K$ in the sample group. $S_K$ has the same meaning in this embodiment as it had in the previous embodiment. If S1 has the greatest value of the sample group, the answer to the question of step 152 will be "yes" and the program passes to step 154. Step 154 asks whether the newest sample point $S_N$, either S6 or S7 depending on the size of the sample group, is less than, or the minimum of, any other sample point $S_j$. $S_j$ also has the same meaning in this embodiment as it had in the previous embodiment. If the newest sample point $S_N$ has the minimum value of the sample points $S_j$, this indicates a generally continuously downward extending curve from S1 to the newest sample point $S_N$, either S6 or S7. In this case, the program passes to step 156 which passes the value of the middle sample point S4 into the video display system 8. Again, the value of register S4 is passed to the video display system 8 as the representative value of the middle of the sample group whether the sample group has 6 or 7 samples as described above in connection with the description of step 96 in the preferred embodiment.

If, in response to step 154, it is determined that the newest sample point $S_N$, S6 or S7, is not less than the other sample points $S_j$, this indicates a generally concave curve formed by the sample group with a minimum value between the end points. In this case, the program passes to step 160 where the minimum value of the sample group is passed to video display system 8.

Returning to step 152, if S1 is not greater than, or the maximum of, any of the other sample points $S_K$, the program passes to step 164.

In step 164, it is determined whether the newest sample point $S_N$, S6 or S7, is greater than, or the maximum of, any other sample point $S_j$. If the newest sample $S_N$, either S6 or S7, is greater than any other sample point $S_j$, the program passes to step 166.

In step 166, it is determined whether S1 is less than or the minimum of any of the other samples $S_K$. If it is, this indicates a generally continuously increasing curve from S1 to the newest sample point $S_N$, either S6 or S7. In response, the program passes to step 156 where the value of the middle sample point S4 is passed to the video display system 8. Once again, the value of S4 is passed as the representative value of the sample group whether the sample group has 6 or 7 sample points as explained above in connection with the description of step 96 in the preferred embodiment.

If, in step 166, the value of S1 is not less than, or the minimum of, any of the other sample points $S_K$, this indicates a generally concave curve and the program passes to step 160 where the program passes the minimum value of the sample group to the video display system 8.

At step 164, if the value of the newest sample point $S_N$, either S6 or S7, is not greater than, or the maximum of, any of the other sample points $S_j$, this indicates that a maximum exists between S1 and either S6 or S7. When this occurs, the program passes to step 162 where the maximum value of the sample points is passed to the video display system 8.

Figure 9:
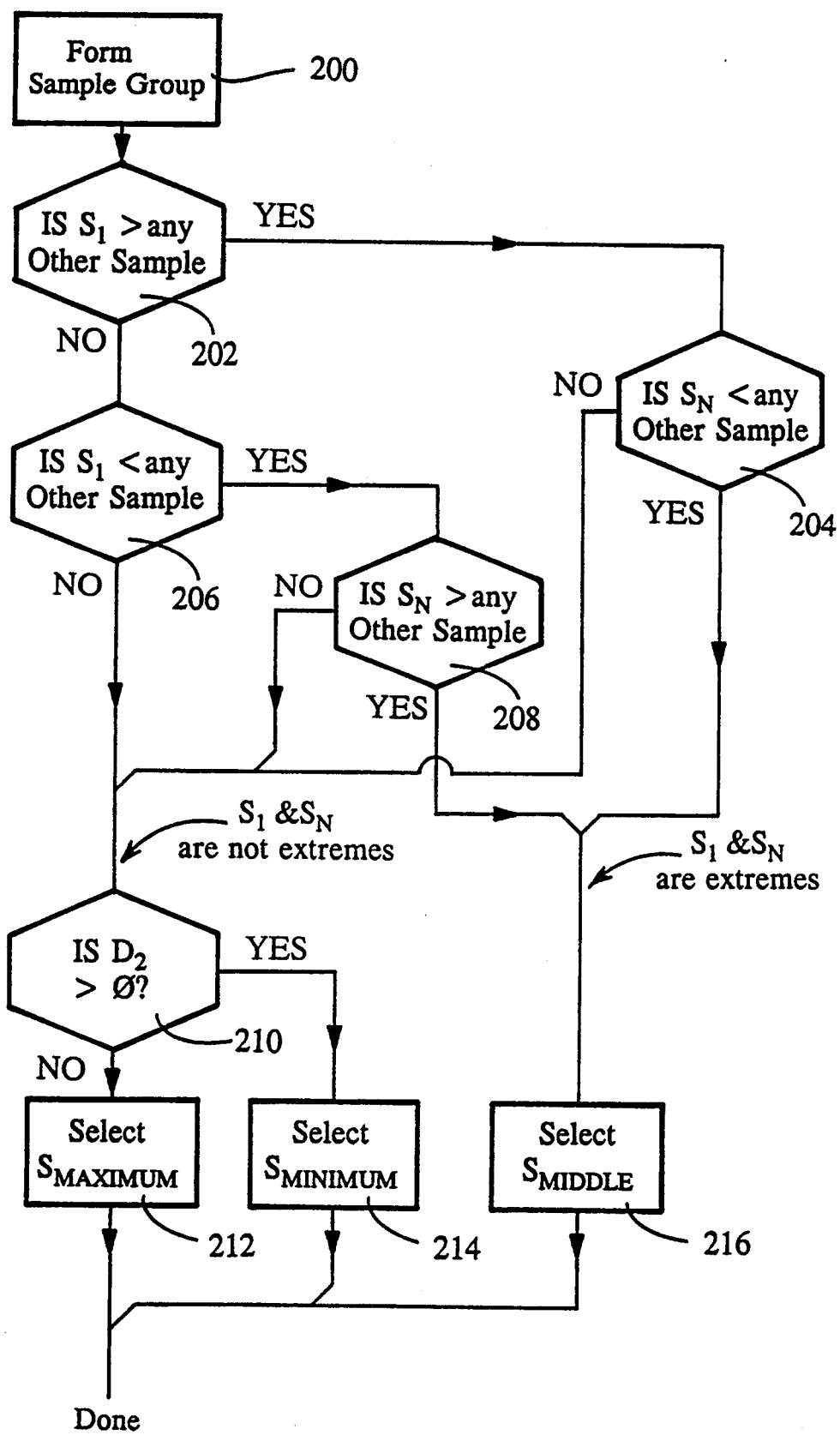
FIG. 9 is a flow chart showing another alternate embodiment of the software of the invention.

An alternate embodiment of the invention is shown in FIG. 9. This alternate flow chart is entered through step 200 which forms a sample group consisting of either 6 or 7 sample points from a sub-group A, B, C, etc. as described above in connection with the description of step 12. The program then passes to step 202.

At step 202 the value of one of the end points of the sub-group, S1, is compared to the values of all the other samples in the sub-group. If the value of end point S1 is larger than the value of any other sample, then the program passes to step 204. At step 204, the value of the other end point of the sample group, $S_N$, is compared to the values of all the other sample points of the sample group to see if the value of end point $S_N$ is smaller than any of the other sample points. If it is, this implies that the value of the first end point S1 is larger than the value of any other sample and the value of the second end point $S_N$ is smaller than the value of any other sample so that the values of the first and second end points S1 and $S_N$ are extreme values for the sub-group. In this case, the program passes to step 216 where the value of the middle sample point S4 of the sub-group is passed to the data processing system such as the video display system 8. The value for S4 is chosen as the value of the middle sample point as explained above in connection with the preferred embodiment.

If, as determined by step 202, the value of the first sample point S1 is greater than the other sample points, which causes the program to pass to step 204, but at step 204 it is determined that the value of the second end point $S_N$ is not smaller than all the values of the other sample points, the program passes to step 210. At step 210, the second derivative of the curve formed by the values of the sample points is calculated. The second derivative is preferably calculated according to the formula set out in detail above in connection with the preferred embodiment. If the second derivative of the sample group is larger than zero, the sub-group is a generally concave group. Therefore, the program passes to step 214 where the minimum value of the sub-group is selected as the value to pass on to the video display system 8. If at step 210 the value of the second derivative of the sample group is not larger than zero, this implies that the sub-group has a generally convex shape. In this case, the program passes to step 212 where the maximum value of the sub-group is passed to the video display system 8.

If at step 202 it is found that the value of the first end point S1 is not larger than all other sample points, the program passes to step 206. At step 206, it is determined whether the value of the first end point S1 is smaller than all other sample points of the sample group. If the value of the first end point S1 is smaller than the value of all other sample points, the program passes to step 208.

At step 208, it is determined whether the value of the second end point $S_N$ is larger than the values of all other sample points. If the value of the second end point $S_N$ is larger than the value of all the other sample points, this implies that the end points S1 and $S_N$ are extreme values of the sub-group. In this case, the program passes to step 216 where the value of the middle sample S4 is passed to the data processing system as described above. If, however, at step 208 the value of the second end point $S_N$ is not larger than the values of any other sample points, this implies that the sub-group has a maximum or minimum value some place between the end points S1 and $S_N$. In this case, the program passes to step 210 for a determination of whether the sample points form a generally concave or convex curve.

As described above, if at step 210 the second derivative of the curve formed by the sample points has a value greater than zero, this implies that the sub-group has a generally concave shape. Therefore, the program passes to step 214 where the minimum value of the sub-group is selected as the representative sample and passed to the data processing system. Again, if at step 210 the second derivative of the curve formed by the sample points has a value not greater than zero, this implies that the sub-group has a generally convex shape. Therefore, the program passes to step 212 where the maximum value of the sub-group is selected as the representative point and passed to the data processing system.

If at step 202 the first end point S1 is not greater than the values of all other sample points and at step 206 the value of the first end point S1 is not less than the value of all other sample points, this implies that the sub-group has a minimum or maximum value between the end points S1 and $S_N$. In this case, the program passes from step 206 to step 210. Again, if at step 210, the second derivative of the curve formed by the sample points has a value greater than zero, this implies that the sub-group has a generally concave shape. Therefore, the program passes to step 214 where the minimum value of the sub-group is passed to the video display system 8. Once again, if the second derivative of the curve formed by the sample points has a value which is not greater than zero, this implies that the sub-group has a generally convex shape. Therefore, the program passes to step 212 where the maximum value of the sub-group is passed to the video display system 8.

Figure 10A:
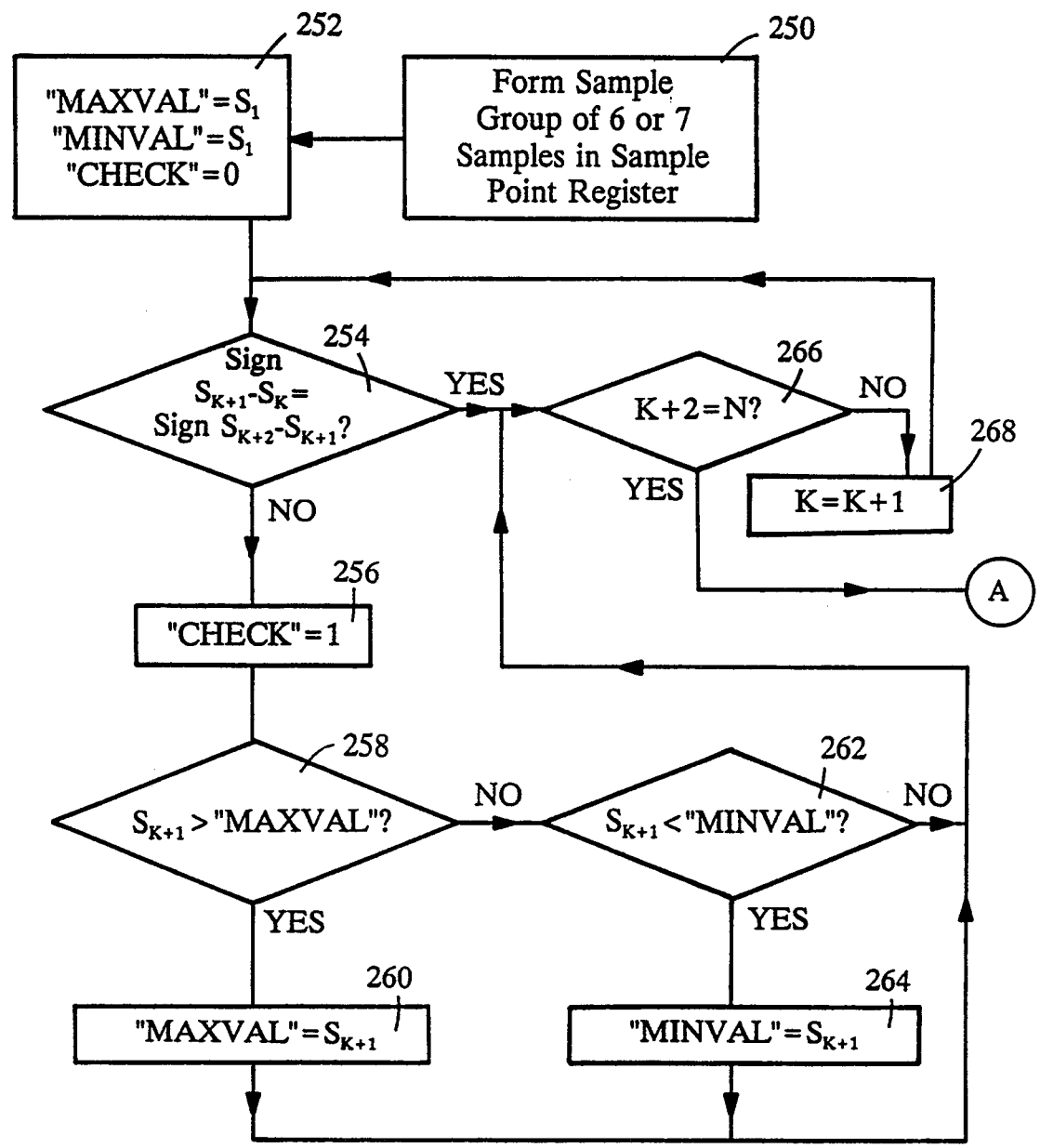
FIG. 10 is a flow chart showing another alternate embodiment of the software of the invention.
Figure 10B:
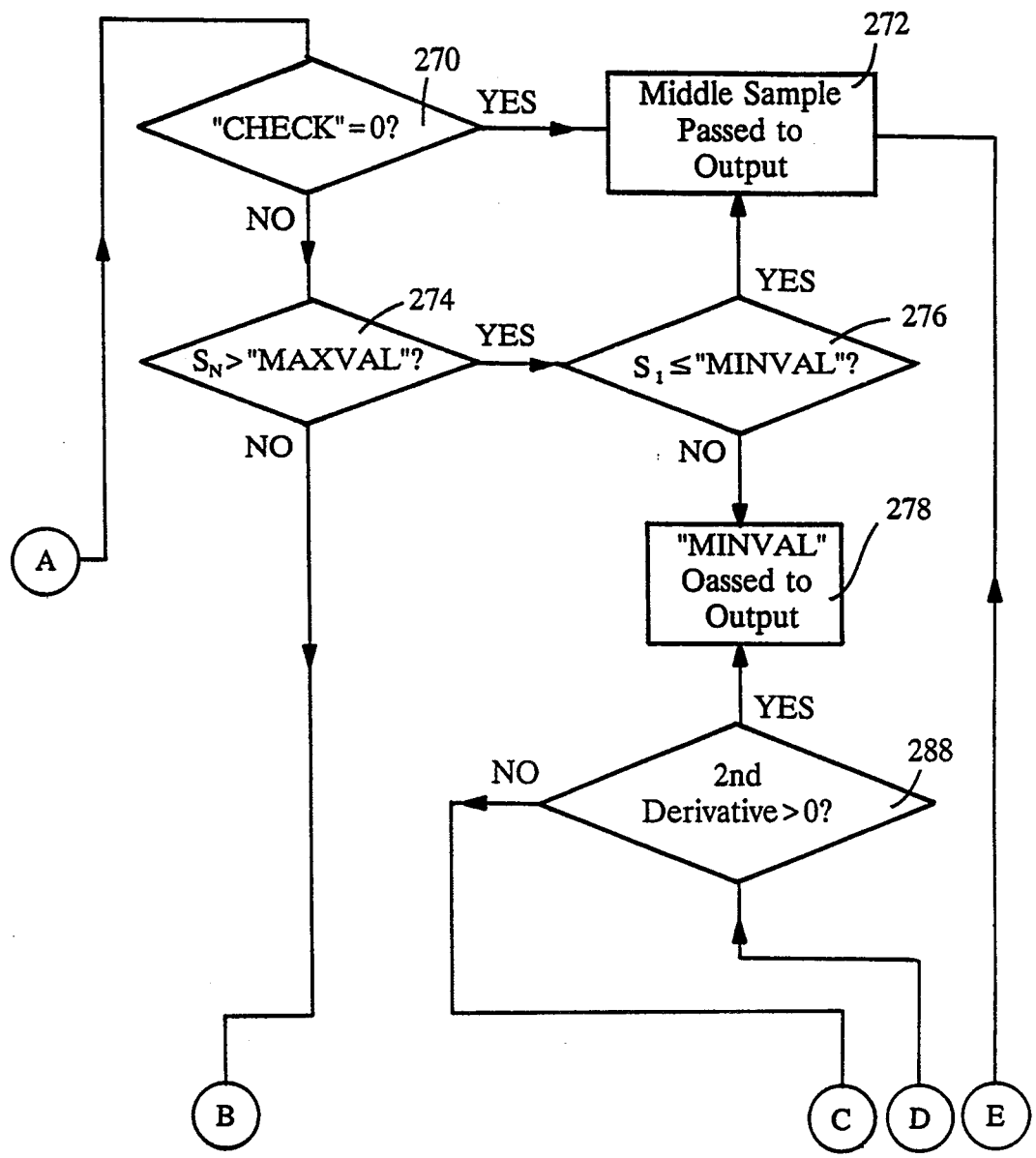
Figure 10C:
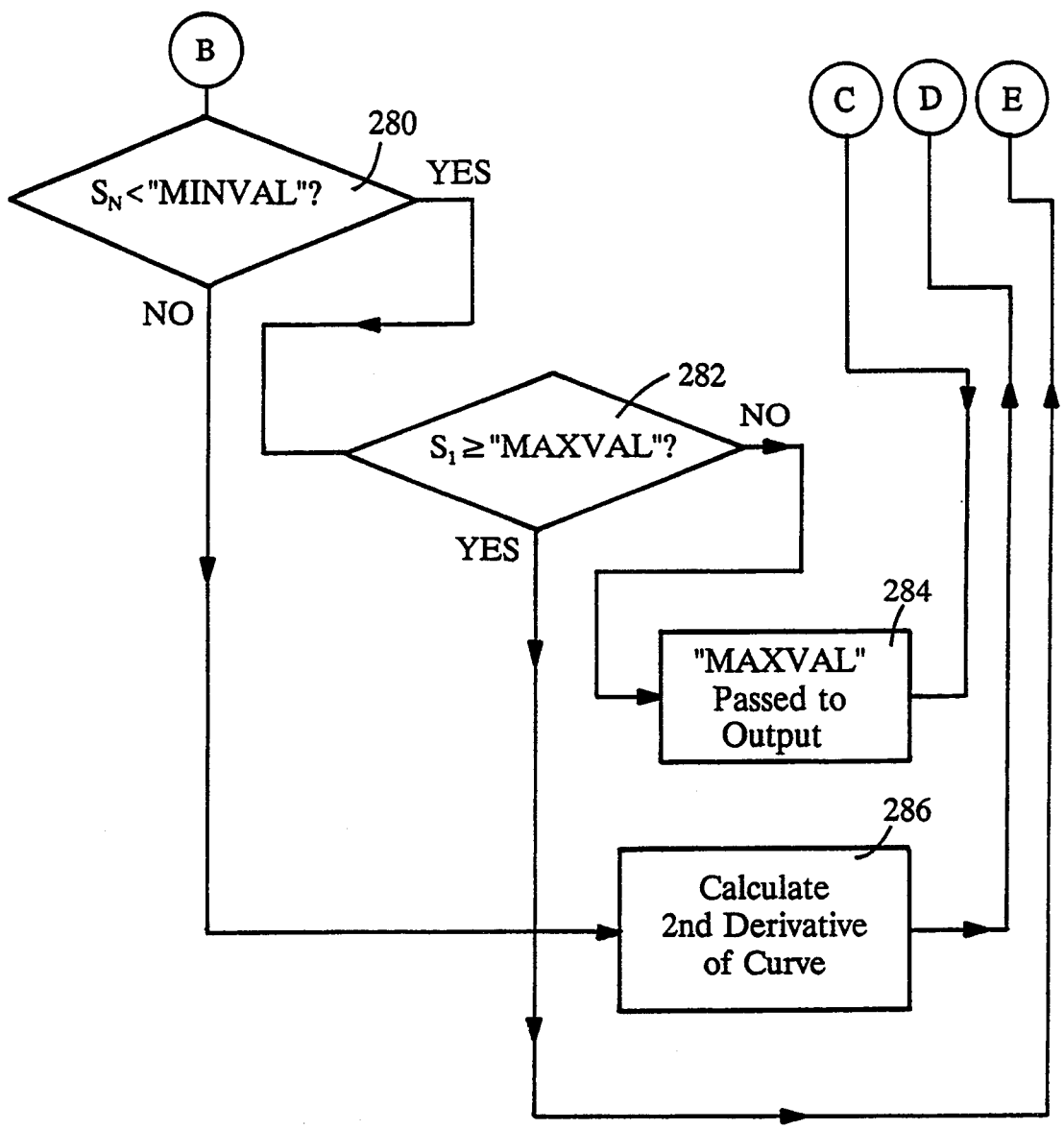

An additional alternative embodiment of the invention uses a calculation of the first derivative of the curve formed by the sample points in combination with a calculation of the second derivative of the curve if necessary, to determine the representative data points for the sample group. This embodiment of the invention is shown in the flow chart of FIG. 10. In FIG. 10, the program begins at step 250 where a sample group of sample points of sub-group A, B, C, etc. consisting of either 6 or 7 sample points are stored in a register as described above in connection with the description of step 12.

Besides the sample point register used to hold the values of the sample points, three additional registers are used in software. A register entitled "MAX VAL" will ultimately contain the maximum value of the samples contained in the sample group. A register entitled "MIN VAL" will ultimately contain the minimum value of the samples in the sample group. A register entitled "CHECK" contains an indicator indicating whether a first derivative equal to zero has been found for a purpose which will be described hereafter. At step 252, the value of the first end point, S1, is placed in registers "MAX VAL" and "MIN VAL". In addition, a 0 is placed in the register "CHECK".

The program then passes to step 254. At step 254, the value of the first derivative of the curve between two sets of consecutive sample points is determined. Specifically, the first derivative of the curve between sample points $S_k$ and $S_{k+1}$, and the first derivative of the curve between sample points $S_{k+1}$ and $S_{k+2}$ is determined where $k=1$ to $N-2$ and $N=$the number of sample points. The value of the first derivative is calculated in the former case by subtracting the value of $S_{k+1}$ from $S_1$ and in the latter by subtracting the value of $S_{k+2}$ from the value of $S_{k+1}$. The value of the first derivative indicates whether the curve between the consecutive points is increasing or decreasing. If the curve is increasing, the value of the derivative of the curve between these consecutive points will be positive. If, however, the value of the first derivative of the curve between the consecutive points is negative, this indicates that the curve between these points is decreasing.

At step 254, once the value of the first derivative between the points $S_k$ and $S_{k+1}$ on one hand and $S_{k+1}$ and $S_{k+2}$ on the other have been determined, the signs of the respective derivatives are compared. If the signs of both sets of derivatives are the same, this indicates that the curve is either constantly increasing or constantly decreasing on the interval from $S_k$ to $S_{k+2}$. In this case, there is no point on the interval $S_k$ to $S_{k+2}$ where the first derivative of the curve is equal to zero. If there is a place on the interval $S_k$ to $S_{k+2}$ where the first derivative of the curve is zero, as indicated by first derivatives of different signs on the former and latter intervals, this indicates the presence of either a local minimum or maximum at the center of the interval at $S_{k+1}$. In this case, the program passes from step 254 to step 256.

Step 256 places the value of "1" in the register "CHECK" to indicate that a local minimum or maximum has been found on the sample group between the end points. Later, as the program progresses, the value stored in the register "CHECK" will be used to determine whether a representative value may be immediately passed to the video display system 8 or whether the program needs to pass to a part of the program for determining the appropriate representative value as will be described in detail hereafter. From step 256 the program passes to step 258.

At step 258, the value of sample point $S_{k+1}$ is compared to the value stored in register "MAX VAL". If the value of the point $S_{k+1}$ is larger than the value stored in the register "MAX VAL" the program passes to step 260 where the value of $S_{k+1}$ is placed in the register "MAX VAL". Thereafter, the program passes from step 260 to step 266.

If, however, at step 258, $S_{k+1}$ is not greater than the value stored in the register "MAX VAL", the program passes to step 262. At step 262, the value of the point $S_{k+1}$ is compared to the value stored in the register "MIN VAL". If the value of the $S_{k+1}$ is less than the value stored in the register "MIN VAL" the program passes to step 264 where the value of $S_{k+1}$ is placed in register "MIN VAL". Thereafter, the program passes to step 266. If, at step 262, the value of $S_{k+1}$ is not less than the value stored in the register "MIN VAL" the program passes to step 266.

The purposes of steps 258 through 264 is to ensure that maximum or minimum value of the local maximum or minimum, respectively, found on the interval $S_k$ through $S_{+2}$ is compared to the maximum and minimum value already determined by the sample group. This ensures that if a local maximum or minimum is found, and if the local maxima or minima is also the absolute maximum or minimum, respectively, determined so far, that this absolute minimum or maximum value is preserved. This is particularly important, where as here, in order to get to steps 258 through 264, a local maximum or minimum had to have occurred between the end points. In any case, the program passes from steps 258 through 264 to step 266. At step 266, the value of $k+2$ is compared to N, which represents the number of sample points making up the sample group. If the value of $k+2=N$, then the program has passed along the sample group to the last sample value. In other words, every derivative for consecutive pairs of sample groups has already been calculated. Therefore, the program passes from step 266 to step 270. If, however, the value of $k+2$ does not $=N$, then the program passes to step 268.

At step 268, because there remains additional sets of consecutive sample points which have not yet had their first derivatives compared, the value of k is incremented by 1. From step 268, the program passes again to step 254 to calculate the first derivatives on the new intervals as described above. The loop formed by steps 266, 268 and 254 ensures that consecutive pairs of sample points will have their first derivatives compared in the sequential fashion starting from the oldest end point and progressing to the newest end point. Then as described above, when $k+2=N$ so that the last set of consecutive sample points have had their first derivatives compared, the program passes to step 270.

Step 270 looks at the value stored in register "CHECK". If the value stored in register "CHECK" equals 0, this indicates that no local maximum or minimum was found between the end points. In other words, the curve between the end points was either monotonically increasing or decreasing between the end points. Therefore, the program passes to step 272 where the value of the middle sample, S4, is passed to the video display system 8 as the representative sample. Step 270 avoids having to go through the comparatively complicated process hereafter to determine the appropriate representative value to pass to the video display system 8 for the special case where there is a continuously increasing or decreasing curve between the first and last end point. In this way, excessive or redundant calculations are avoided.

If at step 270, the value in register "CHECK" equals 1, this indicates that a local minimum or maximum was found somewhere between the end points. In this case, the program passes from step 270 to step 274. At step 274, it is determined whether the value of $S_N$, which is either S6 or S7 in the preferred embodiment, is larger than the value stored in register "MAX VAL". The value of $S_N$ is compared to the value stored in register "MAX VAL" because the value of the last end point, $S_N$, has not yet been compared to the value of the register "MAX VAL". The program heretofore has only compared the value of $S_{k+1}$ to either the register "MAX VAL" or register "MIN VAL". Since $S_N$ can never be $S_{k+1}$, the value of $S_N$ is compared at step 274 to the value stored in register "MAX VAL".

If the value of $S_N$ is larger than the value stored in the register "MAX VAL" the program passes to step 276. At step 276, it is determined whether the value of the first end point, S1, is less than or equal to the minimum value. If the answer is "yes", this indicates that the curve represented by the data points of the sample group is a continuously rising curve from S1 to S7. Therefore, the program passes to step 272 where the value of middle sample, S4, is passed to the video display system 8 as a representative data point. If at step 276 it is found that the value of the first end point, S1, is not equal to or less than the value stored in register "MIN VAL", this indicates that the minimum value of the sample points occurs between the first and last end point. In this case, the program passes from step 276 to step 278 where the value stored in register "MIN VAL" is passed to the video display system as the representative data point.

At step 274, if the value of $S_N$ is not larger than the value stored in register "MAX VAL" the program passes to step 280. At step 280, it is determined whether the value of $S_N$ is smaller than the value stored in register "MIN VAL". Again, for the reason stated above in connection with step 274, the value of $S_N$ is compared to the value stored in register "MIN VAL" because in the program heretofore, the value of $S_N$ could never be the value of $S_{k+1}$ which was previously the value evaluated to see whether it should be placed in the register "MIN VAL". Therefore, at step 280, if the value of $S_N$ is smaller than the value stored in the register "MIN VAL", the program passes to step 282. At step 282, it is determined whether the value of the first end point, S1, is greater than or equal to the value stored in register "MAX VAL". If the answer is "yes", this indicates that the curve formed by the sample points is a continuously decreasing curve from the first end point to the last end point. Therefore, the program passes from step 282 to step 272 where the value of the middle sample point, S4, is passed to the video display system 8 as the representative data point.

If, at step 282, the maximum value of the sample group does not appear at the first end point so that the answer to the question of step 282 is "no", the program passes from step 282 to step 284 where the value stored in the register "MAX VAL", which represents the maximum value of the data points, is passed to the video display system 8 as the representative data point.

If at step 280, the value of the newest end point, $S_N$, is not less than the value stored in register "MIN VAL", the program passes to step 286. At step 286, the second derivative of the sample group is calculated according to the formula given above in connection with the preferred embodiment of the software. The program then passes to step 288 where it is determined whether the second derivative calculated in step 286 is greater than zero. If it is, this indicates that the curve is generally concave and the program passes to step 278 where the value stored in register "MIN VAL", which represents the minimum value of the sample points, is passed to the video display 8 as the representative data point.

If at step 288, the second derivative calculated by step 286 is not greater than zero, this indicates that the curve is generally convex. In this case, the program passes to step 284 where the value stored in register "MAX VAL" is passed to the video display system 8 as the representative data point of the sample group.

Although, in this embodiment, the register "CHECK" contains values of 0 and 1 to indicate whether the curve is a continuously increasing or decreasing curve between the end points or whether a local minimum or maximum occur between the end points, any other indicator indicating these two conditions can be substituted for the use in the register "CHECK".

Figure 1:
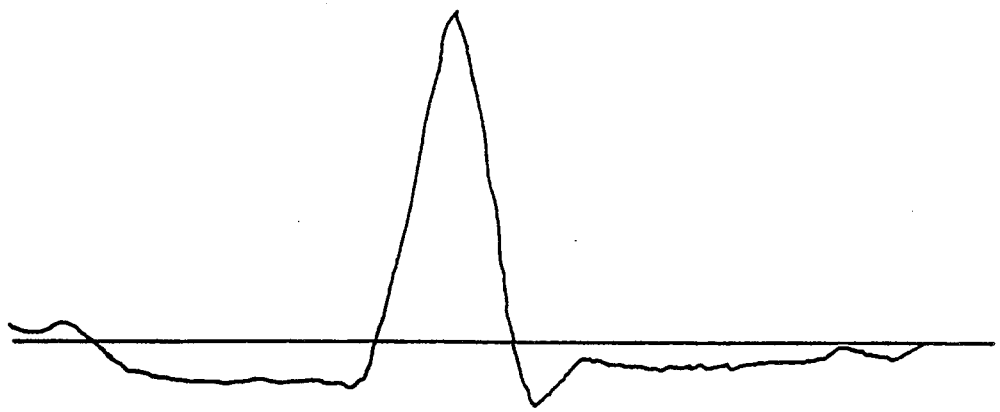
FIG. 1 is a representation of a QRS signal sampled at a rate of 500 samples per second.
Figure 2:
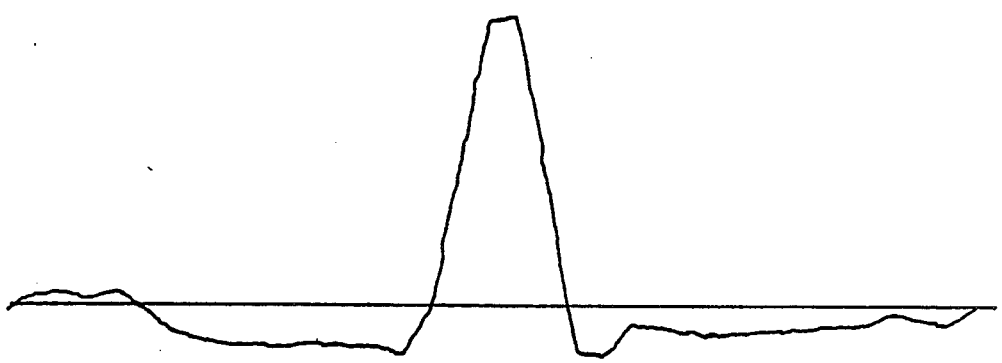
FIG. 2 is a representation of a QRS signal sampled at a rate of 111 samples per second.
Figure 3:
FIG. 3 is a representation of a QRS signal originally sampled at 500 samples per second and subsequently modified by the instant invention to produce sample points at the rate of 111 sample points per second.

FIG. 3 shows the signal sampled at 500 samples per second, as shown in FIG. 1, after being processed by the instant invention and sent to the video display system 8 at a rate of 111 data points per second. As can be seen, the representative ECG signal of FIG. 3 closely resembles the original input ECG signal of FIG. 1.

The instant invention has been described in connection with the preferred and four alternate embodiments where two representative data points for nine consecutive sample points are produced which data points are representative of the values contained on the sub-groups. It is also within the scope of this invention to be applied to sample groups of a larger or smaller size than 9 sample points. In addition, it is within the scope of this invention to provide one or more than two representative data points for the sample group. In the latter case, the sample group may be broken into whatever number of sub-groups it is desired in order to produce the desired number of representative data points. The sub-groups will necessarily contain either an even or odd number of sample points. Depending on whether these sub-groups contain an even or a odd number of sample groups, the invention described above may be modified to incorporate the different sized sub-group by modifying the software by analogy to the description contained above for the sample size of either 6 or 7 sample points as will be clear to those skilled in the art.

With respect to the case where a single representative data point is passed to the video display system 8 or comparable device for the sample group, the process of determining the single representative data point is very similar to that described above in connection with returning a representative data sample point for a sub-group. In this case, the entire sample group may be considered a sub-group of a larger "super" sample group. From this it can be seen that the size of the sample groups or sub-groups and the number of representative data points returned from such sample groups or sub-groups is determined by the requirements of the sampling system and the video display system. In this regard, the sample group may be broken into a required number of sub-groups as described above which sub-groups may be processed to produce representative data points according to the teachings of this invention.

The invention has been described herein in connection with certain specified comparisons between sample points. For example, in the preferred embodiment of the invention, comparisons between the values of the sample points of the sample group and the end points are described as comparing the values of the sample points to the value of the end point labeled S1. By following the flow chart of FIG. 6A-E, it is seen that ultimately the values of the sample points are compared to the newest sample point, either S6 or S7. However, it will be clear to those skilled in the art that the specific direction of comparing end points to the other sample points is not limited to beginning the comparisons with S1 compared to the other sample points and ending with the other sample point values compared to S6 or S7. Instead, the program may just as effectively begin with comparing the value of the newest sample point, in this case either S6 or S7, with the other values of the sample group and ending with the comparison of these values of the sample group with the oldest sample point, S1. This principal applies as well to the alternate embodiments of the invention described herein.

Also, the various comparisons of the value of the sample points has been described as occurring sequentially moving from one sample point to its neighbor. Although this is the preferred way of moving from one sample point to another, it is not a requirement of the invention that it be done this way. This method is preferred merely because it is a clearly ordered way of moving from one sample point to another. Any other order of moving from one sample point to another will produce the desired results of this invention so long as all the sample points are compared to the values in the respective registers as taught by the invention and the distinction between the end points and the sample points between the end points is maintained.

In addition, although the order of comparing the values of the sample group to values contained in the registers has been described in a pre-specified order, it is clear that such comparisons may be done in any order. For example, in steps 20 through 26, the value of $S_2$ is first compared to the value stored in the register MAX VAL, with its attendant results, and then to the value stored in the register MIN VAL with its attendant results. This order of comparison can be reversed if desired without affecting the operation of the invention. Further, it is clear that such relationships as $S1>S2$ may also be expressed as $S2<S1$.

Also, although the instant invention has been described in connection with taking sample points from an ECG system and producing representative data points for display on a video display system, it is within the scope of this invention to apply to any type of sampling system to produce representative data points for whatever use including, but not limited, to video display systems.

In this regard, the invention has been described as producing representative data points for use by a video display system 8. However, the representative data points may just as easily may be used for other data processing purposes as well, including but not limited to being reproduced on a chart recorder. Of course, the data points may be displayed both on a video display system and a chart recorder, as well as used in any other way such as would be apparent to those skilled in the art.

The process of producing sub-groups described above to produce representative values for "front" and "back" groups has included extending their respective sub-group by one data point into the adjacent "back" or "front" groups respectively to provide continuity in the representative data points. An additional benefit of this overlapping is that the maximum value of the ECG signal will be preserved through the device 10 as a representative data point to be passed to the video display system 8. This is because, as has been seen in this application, there are three types of representative data points which will be passed to the video display system: the maximum value of the sample group; the minimum value of the sample group; and, the value of the middle sample. The value of the middle sample is passed as the representative data value when the curve generally continuously increases or decreases between the end points. The maximum or minimum value of the sample group is passed as the representative data point when a maximum or minimum value of the sample group appears between the end points. Using this system of passing representative data points, if overlapping if sub-groups were not used, in certain cases, the maximum value of the ECG signal, as for example the maximum value of R-wave of the QRS complex, might not get passed to the video display system 8. For example, referring to FIG. 5, if the maximum value of the R-wave appeared at sample point 4 so that the sample points 1–3 were continuously rising to sample point 4, the representative sample point for that sample group would be the middle value of the sample group, not the value of sample point 4 which represents the maximum value of the R-wave. Then, in the next sample group consisting of sample points 5–9 if these sample points formed a curve continuously decreasing, once again the representative data point would be the middle sample point. Consequently, for the sample groups formed by the points 1–4 and the representative data point for the sample group formed by the points 5–9, the middle sample point values would be passed as representative data points. The actual maximum value of the R-wave, found at sample point 4, would never been passed to the video display system 8.

In order to correct this, the sub-groups are extended to overlap these "front" and "back" groups by 1. In the example just given, on the representative value for the sub-group A, the value of sample point 4 would be passed to the video display system 8 as the representative data point since the maximum value of that sub-group appeared between the end points of the sub-group. Thereafter, in sub-group B, the maximum value of the sample group would appear at sample point 4 or at point 4, which would be the end point S1 in this sub-group by definition, because the value of data point 4 is the maximum value of the R-wave of the QRS complex, while the other points in this sub-group B would have values less than the value of point 4. Therefore, the representative data point passed from sub-group B would not be the value of point 4. In any case, the maximum value of the R-wave is passed to the video display system 8 by using the system.

Software implementing the preferred embodiment of the invention as shown in FIGS. 6A–E and described above is contained in Appendix I attached hereto.

It is to be understood that the specific description contained herein is given by means of example and not for the purpose of limitation. Changes and modifications may be made to the system described herein and still be within the scope of the claims of the invention. Further, obvious changes and modifications will occur to those skilled in the art.

APPENDIX I

```
/*----------------------------------------------------------

Written by Victor dePinto
©1991 Quinton Instrument Co. All rights reserved.

----------------------------------------------------------*/ include <dsdef.h>
```

```
/*----------------------------------------------------------------
    This function is to be used when down-sampling, that is converting
    a sequence of samples to a second sequence of samples at a
    lower sampling rate than the original sequence. The purpose is to
    preserve the peak-to-peak value of the signal being down-sampled.

When this function is called, a set of samples of the original signal
    is passed to it, from which this function will select and return
    one sample. In order to work reliably, Each set of samples passed
    must overlap with the preceeding set by one sample interval; e.g.
    When downsampling by a ratio of 10, pass the last 12 samples of the
    original sequence.

The minimum and maximum values of the input sample set are found.
    If the minimum and maximum values of the input sample set are at the
    endpoints (oldest and latest), and the minimum and maximum are
    less than and greater than, respectively, than any other sample
    in the set, the middle point is returned.
    Otherwise, a negative or positive peak is assumed; therefore if
    the second derivative is negative, a positive peak is assumed and
    the maximum value is returned. If the second derivative is positive,
    a negative peak is assumed and the minimum value is returned.
*/ int down_sample(samples, number_of_samples, startndx)
    int samples[];
    int number_of_samples;
    int startndx;
{
int selected_sample;

/* Test for monotonic rising or falling slope. */
if (   endpoint_sample_is_greater(samples, number_of_samples)
    && endpoint_sample_is_least(samples, number_of_samples) )
        selected_sample = samples[number_of_samples >> 1];
else {      /* Test for positive or negative peak. */
    if (second_derivative(samples, number_of_samples) < 0)
            selected_sample = max_sample_value(samples, number_of_samples);
    else
            selected_sample = min_sample_value(samples, number_of_samples);
} return (selected_sample);
}

/*----------------------------------------------------------------
    This function returns TRUE if either endpoint sample is greater in
    value than any other sample in the sample set passed; Otherwise
    FALSE is returned. An endpoint sample is defined as either the
    first sample or the last sample. Note that if an endpoint sample
    has the maximun value and another sample has the same value, FALSE
    is returned.
*/
int endpoint_sample_is_greater(samples, number_of_samples)
    int samples[];
    int number_of_samples;
```

```
{
int j;
int max_sample_value;
int endpoint_value_is_greatest;

max_sample_value = samples[0];
endpoint_value_is_greatest = TRUE;

for (j = 1; j < number_of_samples - 1; ++j) {
    if (samples[j] >= max_sample_value) {
        endpoint_value_is_greatest = FALSE;
        max_sample_value = samples[j];
    }
} if (samples[number_of_samples - 1] > max_sample_value) {
    endpoint_value_is_greatest = TRUE;
    max_sample_value = samples[number_of_samples - 1];
}
return (endpoint_value_is_greatest);
}

/*----------------------------------------------------------------
    This function returns TRUE if either endpoint sample is lower in
    value than any other sample in the sample set passed; Otherwise
    FALSE is returned. An endpoint sample is defined as either the
    first sample or the last sample. Note that if an endpoint sample
    has the minimun value and another sample has the same value, FALSE
    is returned.
*/
int endpoint_sample_is_least(samples, number_of_samples)
    int samples[];
    int number_of_samples;
{
int j;
int min_sample_value;
int endpoint_value_is_least;

min_sample_value = samples[0];
endpoint_value_is_least = TRUE;

for (j = 1; j < number_of_samples - 1; ++j) {
    if (samples[j] <= min_sample_value) {
        endpoint_value_is_least = FALSE;
        min_sample_value = samples[j];
    }
} if (samples[number_of_samples - 1] < min_sample_value) {
    endpoint_value_is_least = TRUE;
    min_sample_value = samples[number_of_samples - 1];
}
return (endpoint_value_is_least);
}

/*----------------------------------------------------------------
```

This function returns the 2nd derivative of a set samples passed to it.
*/
```
int second_derivative(samples, number_of_samples)
    int samples[];
    int number_of_samples;
{
int half_nbr_samples;
int der;

half_nbr_samples = number_of_samples >> 1;
der =     samples[0]
      - samples[half_nbr_samples]
      - samples[number_of_samples - 1 - half_nbr_samples]
      + samples[number_of_samples - 1];
return (der);
}
```

/*----------------------------------------------------------------
   Find the highest value in a set of sample values.
*/
```
int max_sample_value(samples, number_of_samples)
    int samples[];
    int number_of_samples;
{
int j;
int max_sample_value;

max_sample_value = samples[0];

for (j = 1; j < number_of_samples; ++j)
    if (samples[j] > max_sample_value)
        max_sample_value = samples[j];

return (max_sample_value);
}
```

/*----------------------------------------------------------------
   Find the lowest value in a set of sample values.
*/
```
int min_sample_value(samples, number_of_samples)
    int samples[];
    int number_of_samples;
{
int j;
int min_sample_value;
min_sample_value = samples[0];

for (j = 1; j < number_of_samples; ++j)
    if (samples[j] < min_sample_value)
        min_sample_value = samples[j];

return (min_sample_value);
}
```

/*----------------------------------------------------------------
   This function is to be used when down-sampling by a ratio of 5 to 1.
   The purpose is to preserve the peak-to-peak value of the signal
   being down-sampled.

A set of 7 samples must be analyzed when selecting each output sample, because of the necessity of analyzing overlapping sample sets.

The minimum and maximum values of the input sample set are found.
If the minimum and maximum values of the input sample set are at the endpoints (oldest and latest), the middle point is returned.
Otherwise, a negative or positive peak is assumed; therefore if the second derivative is negative, a positive peak is assumed and the maximum value is returned. If the second derivative is positive, a negative peak is assumed and the minimum value is returned.
*/

```
#define TRUE  1
define FALSE 0 down_sample_7(last_samples)
    int last_samples[];   /* Array containing the last 7 samples */
                          /* last_samples[6] is most recent.     */
                          /* last_samples[0] is oldest.          */
{
int second_derivative;
int plot_this_value;
int max_sample, min_sample, middle_sample;
int min_at_endpoint, max_at_endpoint;

/* Process sample 0 */
max_sample = *last_samples;
min_sample = *last_samples;
min_at_endpoint = max_at_endpoint = TRUE;
second_derivative = *(last_samples++);

/* Process sample 1 */
if (*last_samples >= max_sample) {
   max_at_endpoint = FALSE;
   max_sample = *last_samples;
}
if (*last_samples <= min_sample) {
   min_at_endpoint = FALSE;
   min_sample = *last_samples;
}
++last_samples;

/* Process sample 2 */
if (*last_samples > max_sample) {
   max_at_endpoint = FALSE;
   max_sample = *last_samples;
}
else
   if (*last_samples < min_sample) {
       min_at_endpoint = FALSE;
       min_sample = *last_samples;
   }
++last_samples;

/* Process sample 3 */
if (*last_samples < min_sample) {
```

```
      min_at_endpoint = FALSE;
      min_sample = *last_samples;
   }
else
   if (*last_samples > max_sample) {
        max_at_endpoint = FALSE;
        max_sample = *last_samples;
   }
middle_sample = *last_samples;
second_derivative -= *last_samples + *(last_samples++);

/* Process sample 4 */
if (*last_samples > max_sample) {
   max_at_endpoint = FALSE;
   max_sample = *last_samples;
}
else
   if (*last_samples < min_sample) {
        min_at_endpoint = FALSE;
        min_sample = *last_samples;
   }
++last_samples;

/* Process sample 5 */
if (*last_samples < min_sample) {
   min_at_endpoint = FALSE;
   min_sample = *last_samples;
}
else
   if (*last_samples > max_sample) {
        max_at_endpoint = FALSE;
        max_sample = *last_samples;
   }
++last_samples;

/* Process sample 6 (latest sample) */
if (*last_samples > max_sample) {
   max_at_endpoint = TRUE;
   max_sample = *last_samples;
}
else
   if (*last_samples < min_sample) { min_at_endpoint = TRUE;
        min_sample = *last_samples;
   }
second_derivative += *last_samples;

/* Select the value to be plotted. */
if (min_at_endpoint && max_at_endpoint)
    plot_this_value = middle_sample;         /* No peak. Use middle point. */
else
    if (second_derivative < 0)
         plot_this_value = max_sample;        /* Positive peak */
    else
         plot_this_value = min_sample;        /* Negative peak */
```

```
return (plot_this_value);
}
/*--------------------------------------------------------------
  This function is to be used when down-sampling by a ratio of 4 to 1.
*/ down_sample_6(last_samples)
    int last_samples[];   /* Array containing the last 6 samples */
                          /* last_samples[5] is most recent.     */
                          /* last_samples[0] is oldest.          */
{
int second_derivative;
int plot_this_value;
int max_sample, min_sample, middle_sample;
int min_at_endpoint, max_at_endpoint;

/* Process sample 0 */
max_sample = *last_samples;
min_sample = *last_samples;
min_at_endpoint = max_at_endpoint = TRUE;
second_derivative = *(last_samples++);

/* Process sample 1 */
if (*last_samples >= max_sample) {
   max_at_endpoint = FALSE;
   max_sample = *last_samples;
}
if (*last_samples <= min_sample) {
   min_at_endpoint = FALSE;
   min_sample = *last_samples;
}
++last_samples;

/* Process sample 2 */
if (*last_samples > max_sample) {
   max_at_endpoint = FALSE;
   max_sample = *last_samples;
}
else
   if (*last_samples < min_sample) {
       min_at_endpoint = FALSE;
       min_sample = *last_samples;
   }

}
 second_derivative -= *(last_samples++);

/* Process sample 3 */
if (*last_samples < min_sample) {
   min_at_endpoint = FALSE;
   min_sample = *last_samples;
}
else
   if (*last_samples > max_sample) {
       max_at_endpoint = FALSE;
       max_sample = *last_samples;
   }
```

```
middle_sample = *last_samples;
second_derivative -= *(last_samples++);

/* Process sample 4 */
if (*last_samples > max_sample) {
   max_at_endpoint = FALSE;
   max_sample = *last_samples;
}
else
   if (*last_samples < min_sample) {
        min_at_endpoint = FALSE;
        min_sample = *last_samples;
    }
+ +last_samples;

/* Process sample 5 (latest sample) */
if (*last_samples > max_sample) {
   max_at_endpoint = TRUE;
   max_sample = *last_samples;
}
else
   if (*last_samples < min_sample) {
        min_at_endpoint = TRUE;
        min_sample = *last_samples;
    }
second_derivative += *last_samples;

/* Select the value to be plotted. */
if (min_at_endpoint && max_at_endpoint)
    plot_this_value = middle_sample;        /* No peak. Use middle point. */
else
    if (second_derivative < 0)
        plot_this_value = max_sample;       /* Positive peak */
    else
        plot_this_value = min_sample;       /* Negative peak */ return (plot_this_value);
}
```

We claim:

1. A device for converting an input digital electrocardiograph (ECG) signal sampled at a first rate to an output digital ECG signal sampled at a second rate where the first rate is higher than the second rate, the output signal made of a series of representative amplitude values for further processing or display, the output signal being representative of the input signal presented to the device, the input signal made up of a series of N sampled input amplitude values $X_n$ ($n-1$ to N), the output signal preserving the maximum and minimum amplitudes of the input signal on the range of the sampled input amplitude values $X_n$, the output signal presented to an output terminal, the device comprising:

a) means for extracting seriatim N sample amplitude values $X_n$ from an input signal and storing said sample input amplitude values $X_n$ in an electronic memory means, said N sampled input amplitude values $X_n$ having a first amplitude end point and a second amplitude end point at $X_1$ and $X_N$, respectively, and a middle sample;

b) means, implemented on a central processing unit, for determining the shape of a curve formed by plotting said sample input amplitude values versus an indicia representing the order that the sampled input amplitude values were sampled and thereafter sequentially connecting said plotted input amplitude values;

c) means for transferring the amplitude value of said middle sample to the output terminal if both the maximum and minimum amplitude values of said sample group appear at said first and second end points, regardless of order;

d) means for transferring the minimum amplitude value of said sample group to the output terminal if said curve is concave shaped; and, e) means for transferring the maximum amplitude value of said sample group to the output terminal if said curve is convex shaped.

2. The device of claim 1 wherein said means for determining the shape of said curve includes:

a) means, implemented on said central processing unit, for calculating the second derivative of said curve; and, b) means implemented on said central processing unit, for comparing the amplitude values of said first and second end points to the amplitude values of said sample points intermediate said first and second end points and for:
  i) transferring the amplitude value of said middle sample to the output terminal if both the maximum and minimum amplitude values of said sample group appear at said first and second end points, regardless of order;
  ii) transferring the minimum amplitude value of said sample group to the output terminal if both the maximum and minimum amplitude values of said sample group do not appear at said first and second end points and the second derivative of said curve is greater than zero; and,
  iii) transferring the maximum amplitude value of said sample group to the output terminal if both the maximum and minimum amplitude values of said sample group do not appear at said first and second end points and the second derivative of said curve is less than zero.

3. The device of claim 1 wherein said means for determining the shape of said curve includes:
  a) means for storing the maximum amplitude value of said sampled input amplitude values $X_n$, said means for storing the maximum amplitude value initialized to contain the amplitude value of $S_1$;
  b) means for storing the minimum amplitude value of said sampled input amplitude values $X_n$, said means for storing the minimum amplitude value initialized to contain the amplitude value of $S_1$;
  c) means, implemented on said central processing unit, for determining the first derivative of a line formed by plotting the points $S_k$ and $S_{k+1}$ versus an indicia representing the order that the sampled input amplitude values were sampled and thereafter connecting the points $S_k$ and $S_{k+1}$ by a straight line and for determining the first derivative of a line formed by plotting the points $S_{k+1}$ and $S_{k+2}$ versus an indicia representing the order that the sampled input amplitude values were sampled and thereafter connecting the points $S_{k+1}$ and $S_{k+2}$ by a straight line where K varies incrementally from 1 to $N-2$;
  d) means, implemented on said central processing unit, for incrementally comparing the sign of said first derivative of the line formed by connecting the points $S_k$ and $S_{k+1}$ to the sign of said first derivative of the line formed by connecting the points $S_k$ and $S_{k+2}$ where K varies incrementally from 1 to $N-2$;
  e) means, implemented on said central processing unit and enabled when the sign of said first derivative of the line formed by connecting the points $S_k$ and $S_{k+1}$ is different than the sign of said first derivative of the line formed by connecting the points $S_{k+1}$ and $S_{k+2}$, for comparing the amplitude value of $S_{k+1}$ to the amplitude value stored in said means for storing the maximum amplitude value and to the amplitude value stored in said means for storing the minimum amplitude value and, if the amplitude value of $S_{k+1}$ is larger or smaller than the amplitude values stored in said means for storing the maximum amplitude value and to the amplitude value stored in said means for storing the minimum amplitude value, respectively, for replacing the amplitude value stored in said means for storing the maximum amplitude value with the amplitude value of $S_{30\ 1}$ and for replacing the amplitude value stored in said means for storing the minimum amplitude value with the amplitude value of $S_{30\ 1}$, respectively, and then incrementing the value of "k" so that the value of the first derivative may be recalculated;
  f) means, enabled when $k-N-2$, for comparing the amplitude value of $S_N$ to the amplitude value stored in said means for storing the maximum amplitude value;
  g) means, enabled in response to a determination that the amplitude value of $S_N$ is larger than the amplitude value stored in said means for storing the maximum amplitude value, for comparing the amplitude value of $S_1$ to the amplitude value stored in said means for storing the minimum amplitude value and for;
    i) transferring the amplitude value stored in the said means for storing the minimum amplitude value to the output terminal if the amplitude value of $S_1$ is not equal to the amplitude value stored in said means for storing the minimum; and,
    ii) transferring the amplitude value of said middle sample to the output terminal if the amplitude value of $S_1$ is equal to the amplitude value stored in said means for storing the minimum;
  h) means, enabled in response to a determination that the amplitude value of $S_N$ is not larger than the amplitude value stored in said means for storing the maximum amplitude value, for comparing the amplitude value of $S_N$ to the amplitude value stored in said means for storing the minimum amplitude value;
  i) means, enabled if both the amplitude value of $S_N$ is not larger than the amplitude value stored in said means for storing the maximum amplitude value and the amplitude value of $S_N$ is not less than the amplitude value stored in said means for storing the minimum amplitude value, for calculating the second derivative of the curve formed by connecting said sample input amplitude values and for:
    1) transferring the amplitude value stored in the said means for storing the minimum amplitude value to the output terminal if said second derivative is greater than zero;
    2) transferring the amplitude value stored in said means for storing the maximum amplitude value to the output terminal if said second derivative is greater than or equal to zero;
  j) means, enabled if the amplitude value of $S_N$ is not larger than the amplitude value stored in said means for storing the maximum amplitude value and the amplitude value of $S_N$ is less than the amplitude value stored in said means for storing the minimum amplitude value, for comparing the amplitude value of $S_1$ to the amplitude value stored in said means for storing the maximum amplitude value, and for:
    i) transferring the amplitude value stored in the said means for storing the maximum amplitude value to the output terminal if the amplitude value of $S_1$ is not equal to the amplitude value stored in said means for storing the maximum amplitude value;
    ii) transferring the amplitude value of said middle sample to the output terminal if the amplitude value of $S_1$ is equal to the amplitude value stored in said means for storing the maximum amplitude value.

4. The device of claim 3 further comprising:
   a) means, enabled in response to a determination that the sign of the lines formed by connecting the sample point $S_k$ and $S_{k+1}$ is not the same as the sign of the first derivative of the line formed by connecting $S_{k+1}$ and $S_{k+2}$ for $k-1$ to $N-2$ incrementally, for storing an indicator indicating that the sign of the lines formed by connecting the sample point $S_k$ and $S_{k+1}$ is not the same as the sign of the first derivative of the line formed by connecting $S_{k+1}$ and $S_{k+2}$ for $k-1$ to $N-2$ incrementally; and,
   b) means, enabled when $k-N-2$, for transferring the amplitude value of the middle sample of said sample group to the output terminal if said means for storing an indicator does not contain said indicator indicating that the sign of the lines formed by connecting the sample point $S_l$ and $S_{k+1}$ is not the same as the sign of the first derivative of the line formed by connecting $S_{k+1}$ and $S_{k+2}$ for $k-1$ to $N-2$ incrementally.

5. The device of claim 1 wherein said middle sample is $X_{(1+N)2}$ if N is odd.

6. The device of claim 5 wherein said middle sample is $X_m$ if N is even where m is the integer value formed by truncating $(1+N)/2$ to the next lowest integer value.

7. The device of claim 5 wherein said middle sample is $X_m$ if N is even where m is the integer value formed by rounding $(1+N)/2$ up to the next highest integer value.

8. The device of claim 1 wherein said sample input amplitude values $X_n$ are consecutively sampled in time.

9. The device of claim 2 wherein said second derivative is calculated by adding the amplitude values of said first and second amplitude endpoints and then subtracting twice the amplitude value of said middle sample amplitude.

10. The device of claim 3 wherein said second derivative is calculated by adding the amplitude values of said first and second amplitude endpoints and then subtracting twice the amplitude value of said middle sample amplitude.

11. The device of claim 1 wherein said central processing unit is a digital central processing unit.

12. The device of claim 11 wherein said digital central processing unit is a microprocessor.

13. The device of claim 1 wherein said means for extracting and storing includes an analog to digital converter connected to said central processing unit for controlling said analog to digital converter to extract the N pieces of sample input amplitude values at a first sample rate and for controlling said electronic memory means to store said N pieces of sample input amplitude values.

14. The device of claim 2 wherein said means for comparing and transferring includes:
   a) electronic memory means for storing the maximum amplitude value of said sampled input amplitude values $X_n$;
   b) electronic memory means for storing the minimum amplitude value of said sampled input amplitude values $X_n$;
   c) electronic memory means for storing an indicator representative of whether the maximum amplitude value of said sampled input amplitude values $X_n$ appears at one end of said amplitude end points of said sampled input amplitude values $X_n$;
   d) electronic memory means for storing an indicator representative of whether the minimum amplitude value of said sampled input amplitude values $X_n$ appears at one of said amplitude end points of said sampled input amplitude values $X_n$;
   e) means for initially placing the amplitude value of said first amplitude end point in both said means for storing the maximum amplitude value and in said means for storing the minimum amplitude value;
   f) means for initially placing an indicator in both said means for storing an indicator representative of whether the maximum amplitude value appears at one of said amplitude end points and in said means for storing an indicator representative of whether the minimum amplitude value appears at one of said amplitude end points, said indicator representing that a maximum amplitude value and a minimum amplitude value, respectively, appear at one of said amplitude end points of said sampled input amplitude values $X_n$;
   g) means for comparing the amplitude value stored in said means for storing the maximum amplitude value to each of the amplitude values of said sampled input amplitude values $X_k$ exclusive of said first endpoint and, if the amplitude value of the compared said sampled input amplitude value $X_l$ is larger than the amplitude value stored in said means for storing the maximum amplitude value, for:
      1) replacing the amplitude value stored in said means for storing the maximum amplitude value with the amplitude value of the compared said sampled input amplitude value $X_k$; and also,
      2) updating the indicator stored in said means for storing representative of whether the maximum amplitude value of said sampled input amplitude values $X_n$ appears at one of said amplitude end points to indicate that the maximum amplitude value of said sampled input amplitude values $X_n$ does not appear at one of said end points unless the maximum amplitude value of said sampled input amplitude values $X_n$ exclusive of said first amplitude endpoint appears at said second amplitude end point;
   h) means for comparing the amplitude value stored in said means for storing the minimum amplitude value to each of the amplitude values of said sampled input amplitude values $X_k$ exclusive of said first amplitude endpoint and, if the amplitude value of the compared said sampled input amplitude value $X_k$ is smaller than the amplitude value stored in said means for storing the minimum amplitude value, for:
      1) replacing the amplitude value stored in said means for storing the minimum amplitude value with the amplitude value of the compared said sampled input amplitude values $X_k$; and also,
      2) updating the indicator stored in said means for storing representative of whether the minimum amplitude value of said sampled input amplitude values $X_n$ appears at one of said amplitude end points to indicate that the minimum amplitude value of said sampled input amplitude values $X_n$ does not appear at one of said amplitude end points unless the minimum amplitude value of said sampled input amplitude values $X_n$ exclusive of said first amplitude end point appears at said second amplitude endpoint;

i) means for calculating the second derivative of said N sampled input amplitude values $X_n$;

j) means for transferring the amplitude value of said middle sample of said N sampled input amplitude values $X_n$ as the representative data point for said N sampled input amplitude values $X_n$ to the output terminal if both of the following conditions occurs:
  1) said indicator stored in said means for storing representative of whether the minimum amplitude value of said sampled input amplitude values $X_n$ appears at one of said amplitude end points indicates that the minimum amplitude value of said sampled input amplitude values $X_n$ appears at one of said amplitude end points of said sampled input amplitude values $X_n$; and,
  2) said indicator stored in said means for storing representative of whether the maximum amplitude value of said sampled input amplitude values $X_n$ appears at one of said amplitude end points indicates that the maximum amplitude value of said sampled input amplitude values $X_n$ appears of one of said amplitude end points of said sampled input amplitude values $X_n$;

k) means for transferring the amplitude value stored in said means for storing the maximum amplitude value to the output terminal as the representative data point for said N sampled input amplitude values $X_n$ if either of the following conditions occurs:
  1) a) said indicator in said means for storing representative of whether the minimum amplitude value of said sampled input amplitude values $X_n$ appears at one of said amplitude end points indicates that the minimum amplitude value of said sampled input amplitude values $X_n$ does not appear at one of said amplitude end points, and,
    b) said second derivative is less than zero;
  2) said indicator in said means for storing representative of whether the minimum amplitude value of said sampled input amplitude values $X_n$ appears at one of said amplitude end points indicates that the minimum amplitude value of said sampled input amplitude values $X_n$ does appear at one of said amplitude end points; and,
    b) said indicator in said means for storing representative of whether the maximum amplitude value of said sampled input amplitude values $X_n$ appears at one of said amplitude end points indicates that the maximum amplitude value of said sampled input amplitude values $X_n$ does not appear at one of said amplitude end points; and,
    c) said second derivative is less than zero;

l) means for transferring the amplitude value stored in said means for storing the minimum amplitude value to the output terminal as the representative data point for said N sampled input amplitude values $X_n$ if either of the following conditions occurs:
  1) a) said indicator in said means for storing representative of whether the minimum amplitude value of said sampled input amplitude values $X_n$ appears at one of said amplitude end points indicates that the minimum amplitude value of said sampled input amplitude values $X_n$ does not appear at one of said amplitude end points; and,
    b) said second derivative is not less than zero;
  2) said indicator in said means for storing representative of whether the minimum amplitude value of said sampled input amplitude values $X_n$ appears at one of said amplitude end points indicates that the minimum amplitude value of said sampled input amplitude values $X_n$ does appear at one of said amplitude end points; and,
    b) said indicator in said means for storing representative of whether the maximum amplitude value of said amplitude sampled input amplitude values $X_n$ appears at one of said amplitude end points indicates that the maximum amplitude value of said sampled input amplitude values $X_n$ does not appear at one of said amplitude end points; and,
    c) said second derivative is not less than zero.

15. The device of claim 1 wherein said sample group contains a predetermined number of sample points which are part of the immediately prior and immediately later sample groups and wherein said sample group overlaps said immediately prior and immediately later sample groups.

16. The device of claim 15 wherein the predetermined number of sample points is one sample point.

17. A method for converting an input digital electrocardiograph (ECG) signal sampled at a first rate to a digital ECG output signal sampled at a second rate where the first rate is higher than the second rate, the output signal made of a series of representative amplitude values for further processing or display, the output signal being representative of the input signal presented to the device, the input signal made up of a series of N sampled input amplitude values $X_n$ (n—1 to N), the output signal preserving the maximum and minimum amplitudes of the input signal on the range of the sampled input amplitude values $X_n$, the output signal presented to an output terminal, the method comprising the steps of:
  a) extracting seriatim N sample input amplitude values $X_N$ from an input signal and storing said sample input amplitude values $X_n$ in an electronic memory means, said N sampled input amplitude values having a first and a second end point at $X_1$ and $X_N$, respectively, and a middle sample;
  b) determining, on a central processing unit, the maximum and the minimum amplitude values of the N sampled input amplitude values;
  c) determining, on a central processing unit, the shape of a curve formed by plotting said sample input amplitude values versus an indicia representing the order that the sampled input amplitude values were sampled and thereafter sequentially connecting said plotted input amplitude values;
  d) transferring the amplitude value of said middle sample to the terminal if both the maximum and minimum amplitude values of said sample group appear at said first and second end points, regardless of order;
  e) transferring the minimum amplitude value of said sample group to the terminal if said curve is concave shaped; and,
  f) transferring the maximum amplitude value of said sample group to the terminal if said curve is convex shaped.

18. The method of claim 17 wherein said step of determining the shape of said curve includes the steps of:
  a) calculating, on said central processing unit, the second derivative of said sample input amplitude values $X_n$; and, b) comparing, on said central processing unit, the amplitude values of said first and second end points to the amplitude values of said sample input amplitude values intermediate said first and second end points and for:
   i) transferring the amplitude value of said middle sample to the output terminal if both maximum and minimum amplitude values of said sample input amplitude values $X_n$ appear at said first and second end points, regardless of order;
   ii) transferring the minimum amplitude value of said sample input amplitude values to the output terminal if both the maximum and minimum amplitude values of said sample input 19. The method of claim 17 wherein said steps of determining the shape of said curve includes the steps of:
   a) initially storing, in an electronic memory register designated for storing the maximum amplitude value of said sampled input amplitude values $X_n$, the amplitude value of sample $S_1$;
   b) initially storing, in an electronic memory register designated for storing the minimum amplitude value of said sampled input amplitude values $X_n$, the amplitude value of sample $S_1$;
   c) determining, on said central processing unit, incrementally as K varies from 1 to N−2, the first derivative of the line formed by plotting the points $S_k$ and $S_{k+1}$ versus an indicia representing the order that the sampled input amplitude values were sampled and thereafter connecting the points $S_k$ and $S_{k+1}$ by a straight line,
   d) determining, on said central processing unit, incrementally as K varies from 1 to N−2, the first derivative of the line formed by plotting the points $S_{k+1}$ and $S_{k+2}$ versus an indicia representing the order that the sampled input amplitude values were sampled and thereafter connecting the points $S_{k+1}$ and $S_{k+2}$ by a straight line;
   e) comparing, on said central processing unit, incrementally as K varies from 1 N−2, the sign of said first derivative of the line formed by connecting the points $S_k$ and $S_{k+1}$ to the sign of said first derivative of the line formed by connecting the points $S_{k+1}$ and $S_{k+2}$;
   f) storing, in response to a determination that the sign of said first derivative of the line formed by connecting the points $S_k$ and $S_{k+1}$ is different than the sign of said first derivative of the line formed by connecting the points $S_{k+1}$ and $S_{k+2}$ and a determination that the amplitude value of $S_{k+1}$ is larger than the amplitude value stored in said electronic memory register for storing the maximum amplitude value of said sampled input amplitude values $X_n$, the amplitude value of $S_{k+1}$ in said electronic memory register for storing the maximum amplitude value of said sampled input amplitude values $X_n$;
   g) storing, in response to a determination that the sign of said first derivative of the line formed by connecting the points $S_k$ and $S_{k+1}$ is different than the sign of said first derivative of the line formed by connecting the points $S_{k+1}$ and $S_{k+2}$ and a determination that the amplitude value of $S_{k+1}$ is smaller than the amplitude value stored in said electronic memory register for storing the minimum amplitude value of said sampled input amplitude values $X_n$, the amplitude value of $S_{k+1}$ in said electronic memory register for storing the minimum amplitude value of said sampled input amplitude values $X_n$;
   h) comparing, when k−N−2, the amplitude value of $S_N$ to the amplitude value stored in said electronic memory register for storing the maximum amplitude value of said sampled input amplitude values $X_n$;
   i) comparing, in response to a determination that the amplitude value of $S_N$ is larger than the amplitude value stored in said electronic memory register for storing the maximum amplitude value of said sampled input amplitude values $X_n$, the amplitude value of $S_1$ to the amplitude value stored in said electronic memory register for storing the minimum amplitude value of said sampled input amplitude values $X_n$ and:
      A) transferring the amplitude value stored in said electronic memory register for storing the minimum amplitude value of said sampled input amplitude values $X_n$ to the output terminal if the amplitude value of $S_1$ is not equal to the amplitude value stored in said electronic memory register for storing the minimum amplitude value of said sampled input amplitude values $X_n$; and,
      B) transferring the amplitude value of said middle sample to the output terminal if the amplitude value of $S_1$ is equal to the amplitude value stored in said electronic memory register for storing the minimum amplitude value of said sampled input amplitude values $X_n$;
   j) comparing, in response to a determination that the amplitude value of $S_N$ is not larger than the amplitude value stored in said electronic memory register for storing the maximum amplitude value of said sampled input amplitude values $X_n$, the amplitude value of $S_N$ to the amplitude value stored in said electronic memory register for storing the minimum amplitude value of said sampled input amplitude values $X_n$;
   A) calculating, if both the amplitude value of $S_N$ is not larger than the amplitude value stored in said electronic memory register for storing the maximum amplitude value of said sampled input amplitude values $X_n$ and the amplitude value of $S_N$ is not less than the amplitude value stored in said electronic memory register for storing the minimum amplitude value of said sampled input amplitude values $X_n$, the second derivative of the curve formed by connecting said sample input amplitude values and:
      1) transferring the amplitude value stored in said electronic memory register for storing the minimum amplitude value of said sampled input amplitude values $X_n$ to the output terminal if said second derivative is greater than zero;
      2) transferring the amplitude value stored in said electronic memory register for storing the maximum amplitude value of said sampled input amplitude values $X_n$ to the output terminal if said second derivative is greater than or equal to zero;
   k) comparing, if the amplitude value of $S_N$ is not larger than the amplitude value stored in said electronic memory register for storing the maximum amplitude value of said sampled input amplitude values $X_n$ and the amplitude value of $S_N$ is less than the amplitude value stored in said electronic memory register for storing the minimum amplitude value of said sampled input amplitude values $X_n$, the amplitude value of $S_1$ to the amplitude value stored in said electronic memory register for storing the maximum amplitude value of said sampled input amplitude values $X_n$ and:

A) transferring the amplitude value stored in said electronic memory register for storing the maximum amplitude value of said sampled input amplitude values $X_n$ to the output terminal if the amplitude value of $S_1$ is not equal to the amplitude value stored in said electronic memory register for storing the maximum amplitude value of said sampled input amplitude values $X_n$;

B) transferring the amplitude value of said middle sample to the output terminal if the amplitude value of $S_1$ is equal to the amplitude value stored in said electronic memory register for storing the maximum amplitude value of said sampled input amplitude values $X_n$.

20. A device for converting an input electrocardio graph (ECG) signal to an output ECG signal made of a series of representative amplitude values for further processing or display, the output signal being representative of an input ECG signal presented to the device, the input ECG signal made up of a series of N sampled input amplitude values $X_n$ (n−1 to N), the ECG output signal preserving the maximum and minimum amplitudes of the ECG input signal on the range of the sampled input amplitude values $X_n$, the output signal presented to an output terminal, the device comprising:

a) an analog to digital converter for sampling seriatim an input analog ECG signal and for producing N pieces of digital sample input amplitude values $X_n$ from the input ECG signal, the N pieces of sampled input amplitude values $X_n$ having a first and a second end point at $X_1$ and $X_N$, respectively, and a middle sample;

b) random access memory means for storing the digital sample input amplitude values $X_n$, for preserving the order of the sampled input values, and for identifying the middle sample;

c) means, implemented on a central processing unit, for examining the sampled input amplitude values $X_n$ and selecting therefrom a maximum and a minimum amplitude value of the sampled input amplitude values $X_n$;

d) means, implemented on a central processing unit, for determining whether a curve, formed by plotting amplitude values of the sample input amplitude values versus the order the sample input amplitude values were sampled and thereafter sequentially connecting the sample input amplitude values, is concave, convex or straight;

e) means for:

i) transferring the amplitude value of the middle sample to the output terminal if both the maximum amplitude value and the minimum amplitude value of the sample input amplitude values appear at the first and second end points, $X_1$ and $X_N$, respectively, regardless of order;

ii) transferring the minimum amplitude value of the sample input amplitude values to the output terminal if the means for determining whether a curve formed determines that the curve formed is concave shaped; and, iii) transferring the maximum amplitude value of the sample input amplitude values to the output terminal if the means for determining whether a curve formed determines that the curve formed is convex shaped.

21. A method for converting, a digital electrocardiograph (ECG) signal sampled at a first rate to an ECG signal sampled at a second rate where the first rate is higher than the second rate and for preserving the maximum and minimum amplitudes of the digital ECG signal sampled at the first rate in the digital ECG signal sampled at the second rate comprising the steps of:

receiving, at an input terminal, a digital ECG signal sampled at a first sample rate;

examining a seriatim portion of the ECG signal sampled at the first rate and presented to the input terminal, the portion having a beginning endpoint, an ending endpoint and a middle point and determining whether the amplitudes of the portion: are monotonically increasing in amplitude, are monotonically decreasing in amplitude, have a highest amplitude value located between the beginning and the ending endpoints or have a lowest amplitude value located between the beginning and the ending endpoints;

transferring a representative amplitude to an output terminal at a second sample rate that is lower than the first sample rate, the representative amplitude determined in response to the step of determining, the representative amplitude being:

i) the middle point amplitude if the step of determining determines that the amplitudes of the portion are monotonically increasing or monotonically decreasing in amplitude;

ii) the highest amplitude value if the step of determining determines that the highest amplitude value is located between the beginning and the ending endpoints;

iii) the lowest amplitude value if the step of determining determines that the lowest amplitude value is located between the beginning and the ending endpoints;

whereby the series of representative amplitudes transferred to the output terminal by the step of transferring a representative amplitude produces a digital ECG signal that preserves the maximum and minimum amplitudes of the digital ECG signal sampled at the first rate.

22. Apparatus for converting, in real time, a digital electrocardiograph signal sampled at a first rate to an electrocardiograph signal sampled at a second rate where the first rate is higher than the second rate and for preserving the maximum and minimum amplitudes of the digital electrocardiograph signal sampled at the first rate in the digital electrocardiograph signal sampled at the second rate comprising:

an input terminal for receiving the electrocardiograph signal sampled at the first sample rate;

an output terminal for transferring the electrocardiograph signal sampled at the second sample rate to a video display device for display;

means, attached to the input terminal, for examining a seriatim portion of the electrocardiograph signal sampled at the first rate, the portion having a beginning endpoint, an ending endpoint and a middle point, and for determining whether the amplitudes of the portion: are monotonically increasing in amplitude, are monotonically decreasing in amplitude, have a highest amplitude value located between the beginning and the ending endpoints, or have a lowest amplitude value located between the beginning and the ending endpoints;

means for transferring a representative amplitude to the output terminal at the second sample rate that is lower than the first sample rate, the second sample rate being the rate required to provide amplitudes to a video display device for display, the representative amplitude determined in response to the determination of the means for examining and determining, the representative amplitude being:
   i) the middle point amplitude if the means for examining and determining determines that the amplitude of the portion are monotonically increasing or monotonically decreasing in amplitude;
   ii) the highest amplitude value if the means for examining and determining determines that the highest amplitude value is located between the beginning and the ending endpoints;
   ii) the lowest amplitude value if the means for examining and determining determines that the lowest amplitude value is located between the beginning and the ending endpoints.

23. Apparatus for converting analog electrocardiograph (ECG) signals to an ECG signal sampled at a rate compatible with external devices comprising:

an input terminal for receiving the analog ECG input signal;

means for sampling the analog ECG input signal at a first rate and for producing a digital ECG input signal;

an output terminal for transferring the digital ECG signal to an external device;

means, attached to the means for sampling, for examining a seriatim portion of the ECG signal sampled at the first rate, the portion having a beginning endpoint, and ending endpoint and a middle point, and for determining whether the digital amplitudes of the portion: are monotonically increasing in amplitude, are monotonically decreasing in amplitude, have a highest amplitude value located between the beginning and the ending endpoints, or have a lowest amplitude value located between the beginning and the ending endpoints;

means for transferring a representative amplitude to said output terminal at a second sample rate for transferring the electrocardiograph signal sampled at the second sample rate to an external device for further processing or display, the representative amplitude value determined in response to the determination of the means for examining and determining, the representative amplitude being:
   i) the middle point amplitude if the means for examining and determining determines that the digital amplitudes of the portion are monotonically increasing or monotonically decreasing in amplitude;
   ii) the highest amplitude value if the means for examining and determining determines that the highest amplitude value is located between the beginning and the ending endpoints;
   iii) the lowest amplitude value if the means for examining and determining determines that the lowest amplitude value is located between the beginning and the ending endpoints.

* * * * *

UNITED STATES PATENT AND TRADEMARK OFFICE
CERTIFICATE OF CORRECTION

PATENT NO. : 5,365,428
DATED : November 15, 1994
INVENTOR(S) : dePinto et al.

It is certified that error appears in the above-indentified patent and that said Letters Patent is hereby corrected as shown below:

In column 6, line 40, after "If S2 is not" insert --less--.

In column 6, line 48, after "Steps" and before "through 38" insert --30--.

In column 7, line 38, replace "86" with --82--.

In column 8, line 17, replace "greater" with --less--.

In column 14, line 45, replace "curvet" with --curve,--.

In column 36, lines 4 and 6, replace "$S_{30\ 1}$" with --$S_{k+1}$--.

In column 36, line 10, replace "k-N-2" with --K=N-2--.

In column 37, line 7, after "sign" insert --of the first derivative--.

In column 37, line 15, replace "k-1" with --K=1--.

In column 37, line 16, replace "k-N-2" with --K=N-2--.

In column 37, line 21, replace "$S_1$" with --$S_k$--.

In column 37, line 23, replace "k-1" with --K=1--.

In column 37, line 26, replace "$X_{(1+N)2}$" with --$X_{(1+N)/2}$--.

In column 41, line 42, after "1" insert --to--.

In column 42, line 5, replace "k-N-2" with --K=N-2--.

UNITED STATES PATENT AND TRADEMARK OFFICE
CERTIFICATE OF CORRECTION

PATENT NO. : 5,365,428
DATED : November 15, 1994
INVENTOR(S) : dePinto et al.

It is certified that error appears in the above-indentified patent and that said Letters Patent is hereby corrected as shown below:

In column 43, line 66, before "formed" insert --is--.(first occurrence)

In column 44, line 3, before "formed" insert --is--.(first occurrence)

In column 44, line 5, after "converting" delete the comma.

In column 44, line 12, before "receiving" insert --a) --.

In column 44, line 14, before "examining" insert --b) --.

In column 44, line 25, before "transferring" insert --c) --.

Signed and Sealed this

Seventeenth Day of October, 1995

Attest:

BRUCE LEHMAN

Attesting Officer

Commissioner of Patents and Trademarks